US010039536B2

(12) United States Patent
Masters et al.

(10) Patent No.: US 10,039,536 B2
(45) Date of Patent: Aug. 7, 2018

(54) IMPLANTABLE MEDICAL DEVICE DEPLOYMENT SYSTEM

(71) Applicant: W. L. Gore & Associates, Inc., Newark, DE (US)

(72) Inventors: Steven J. Masters, Flagstaff, AZ (US); Thomas R. McDaniel, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 52 days.

(21) Appl. No.: 14/070,084

(22) Filed: Nov. 1, 2013

(65) Prior Publication Data

US 2014/0142621 A1  May 22, 2014

Related U.S. Application Data

(60) Provisional application No. 61/798,500, filed on Mar. 15, 2013, provisional application No. 61/727,550, filed on Nov. 16, 2012.

(51) Int. Cl.
*A61F 2/06* (2013.01)
*A61B 17/00* (2006.01)
(Continued)

(52) U.S. Cl.
CPC .... *A61B 17/0057* (2013.01); *A61B 17/12109* (2013.01); *A61B 17/12122* (2013.01); *A61B 17/12177* (2013.01); *A61B 2017/00575* (2013.01); *A61B 2017/00579* (2013.01); *A61B 2017/00592* (2013.01);
(Continued)

(58) Field of Classification Search
CPC .......... A61B 17/0057; A61B 17/12109; A61B 17/12122; A61B 2017/00575; A61B 2017/00579; A61B 2017/00592; A61B 2017/00597; A61B 2017/00601; A61B 2019/4836; A61B 2017/12054; A61B 2017/00623; A61B 2017/00606; A61B 2017/00619; A61B 2017/00867;
(Continued)

(56) References Cited

U.S. PATENT DOCUMENTS 5,853,422 A   12/1998 Huebsch et al.
6,102,942 A   8/2000 Ahari
(Continued)

FOREIGN PATENT DOCUMENTS

JP   2001523686 A   8/2007
JP   2007526087 A   9/2007
(Continued)

OTHER PUBLICATIONS

International Search Report for PCT/US2013/069609 dated Mar. 19, 2014, corresponding to U.S. Appl. No. 14/070,084, 6 pages.

*Primary Examiner* — Elizabeth Houston
*Assistant Examiner* — Mohamed Gabr

(57) ABSTRACT

A medical device delivery system includes an implantable medical device and a delivery device. The implantable medical device includes at least one attachment feature having an elastomeric element. The delivery device includes a catheter and an elongate element. The catheter is arranged to contact the elastomeric element, and the elongate element is arranged to releasably couple with the elastomeric element.

15 Claims, 14 Drawing Sheets

(51) Int. Cl.
*A61B 17/12* (2006.01)
*A61B 90/00* (2016.01)

(52) U.S. Cl.
CPC ............... *A61B 2017/00597* (2013.01); *A61B 2017/00601* (2013.01); *A61B 2017/00623* (2013.01); *A61B 2017/12054* (2013.01); *A61B 2090/0807* (2016.02)

(58) Field of Classification Search
CPC .......... A61F 2002/011; A61F 2002/015; A61F 2002/018; A61F 2/01
USPC ....................................................... 623/1.11
See application file for complete search history.

(56) References Cited

U.S. PATENT DOCUMENTS

| | | | |
|---|---|---|---|
| 7,318,833 B2 | 1/2008 | Chanduszko | |
| 7,678,123 B2 | 3/2010 | Chanduszko | |
| 7,871,419 B2 | 1/2011 | Devellian et al. | |
| 8,257,389 B2 | 9/2012 | Chanduszko et al. | |
| 2003/0150821 A1 | 8/2003 | Bates et al. | |
| 2005/0038470 A1* | 2/2005 | van der Burg | A61B 17/0057 606/213 |
| 2005/0043759 A1* | 2/2005 | Chanduszko | 606/213 |
| 2005/0267523 A1* | 12/2005 | Devellian | A61B 17/0057 606/213 |
| 2007/0250081 A1* | 10/2007 | Cahill et al. | 606/151 |
| 2007/0293928 A1 | 12/2007 | Tomlin | |
| 2008/0086168 A1* | 4/2008 | Cahill | A61B 17/0057 606/213 |
| 2012/0172927 A1* | 7/2012 | Campbell et al. | 606/213 |

FOREIGN PATENT DOCUMENTS

| | | |
|---|---|---|
| JP | 2009532123 A | 9/2009 |
| WO | 03/073961 | 9/2003 |
| WO | 03/094748 | 11/2003 |
| WO | 2005006990 A2 | 1/2005 |
| WO | 2005092203 A1 | 10/2005 |
| WO | 2007/115117 | 10/2007 |
| WO | 2008/042229 | 4/2008 |

* cited by examiner

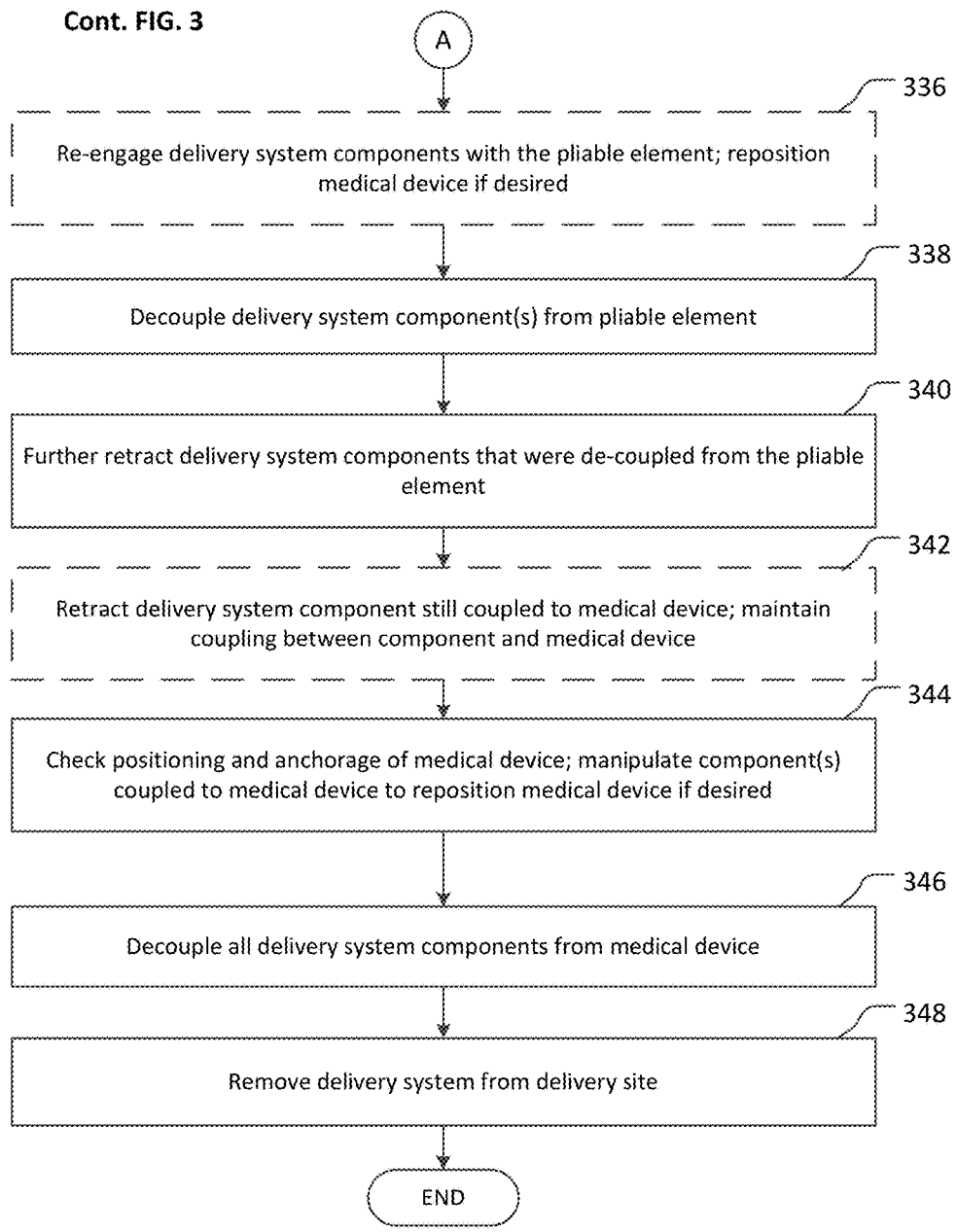

IMPLANTABLE MEDICAL DEVICE DEPLOYMENT SYSTEM

TECHNICAL FIELD

This document relates to deployment systems and methods that are useful, for example, for controllably deploying implantable medical devices in desired positions within bodily cavities, organs, and vessels.

BACKGROUND

A wide variety of known medical devices can be implanted within a patient's body to provide interventional or remedial treatments. Occlusion devices, for example, can be implanted to close perforations in septa. An atrial septal defect (ASD) in the heart is an abnormal opening in the septum between the left and right atria of the heart, and is one such condition that can be treated by implanting an occlusion device. A ventricular septal defect (VSD) in the heart is an abnormal opening in the septum between the left and right ventricles of the heart, and is another condition that can be treated by implanting an occlusion device.

Occlusion devices can also be implanted to block or occlude undesired conduits, fistulae, or ostia. For example, the left atrial appendage (LAA) is a closed cavity that looks like a small thumb or windsock, and is connected to the anterolateral wall of the left atrium between the mitral valve and the root of the left pulmonary vein. The LAA contracts with the left atrium during a normal heart cycle and keeps blood therein from becoming stagnant. However, with atrial fibrillation, the LAA often fails to contract with any vigor due to disorganized electrical signals. As a result, thrombi can be predisposed to form in the stagnant blood within the LAA. An implantable medical device can be used to block off the LAA to prevent an escape of thrombi from the LAA, preventing introduction of the thrombi to an individual's vasculature. Other types of known medical devices can be also implanted in patients to treat a wide variety of disorders.

Many implantable medical devices are delivered to a deployment site using minimally invasive transcatheter techniques. In such cases, the medical device is typically configured in a collapsed arrangement and delivered to the internal deployment site via a delivery sheath. At the deployment site, the medical device is ejected from the sheath and expands to a larger size to provide effective treatment of the particular medical condition, such as occluding an ASD, VSD, or LAA. In some cases, a delivery catheter is attached to the implantable medical device and is used to advance the collapsed implantable medical device through the delivery sheath to the deployment site.

One example delivery system attaches the delivery catheter to the implantable medical device via a threaded screw-type attachment. For example, the implantable medical device may include a female threaded receptacle that is configured to receive a male threaded portion of the delivery catheter, and the delivery catheter is attached to the medical device in this manner. After the implantable device is deployed from the delivery sheath at the deployment site, a clinician operator provides a rotational force at a proximal end of the delivery catheter to cause the delivery catheter to unscrew, and detach, from the implantable device.

SUMMARY

A deployment system and methods are described herein that are useful, for example, for controllably deploying implantable medical devices in desired positions within bodily cavities, organs, and vessels. The systems and methods provided herein can be used for transcatheter deployment of implantable medical devices. In an example embodiment, a deployment system and method for deploying an implantable medical device comprising a self-expanding frame with a covering is provided.

Particular embodiments of the subject matter described in this specification can be implemented so as to realize one or more of the following advantages. An implantable medical device having one or more attachment features can be deployed in controlled manner such that the medical device can be accurately positioned and released as desired by a clinician operator using a deployment system that is releasably coupled to the one or more attachment features. An implantable medical device can be temporarily released from the deployment system, the device can seek a conforming deployed position, and the deployment system can be re-coupled to the device if repositioning of the device by manipulation of the deployment system is desired. The deployment system provided can be used to accurately control the positioning of an implantable medical device without being overly complex for a clinician operator to operate.

In one general aspect, this document provides a medical device delivery system. The medical device delivery system comprises an implantable medical device and a delivery device. The implantable medical device includes a first attachment feature disposed near a distal end of the device and a second attachment feature. The first attachment feature includes an elastomeric element. The delivery device includes a first catheter that is arranged to pass through the second attachment feature and contact the elastomeric element, and an elongate element that is arranged to releasably couple with the elastomeric element.

In various implementations, the elastomeric element may include a channel that extends in an axial direction through the elastomeric element. The elongate element may include a bulbous tip at the distal end of the elongate element. The bulbous tip may be adapted to pass through the channel. The delivery system may further comprise a delivery sheath. The implantable medical device and the delivery device may be capable of being located in one or more lumens of the delivery sheath. The delivery system may further comprise a deployment actuator coupled to the delivery device and to the delivery sheath. The deployment actuator may be adapted to control positioning of the implantable medical device. The second attachment feature may be near a proximal end of the device. The elastomeric element may be fixedly attached to the first attachment feature. A distal end of the first catheter may be arranged to abut against the elastomeric element. The second attachment feature may define an aperture through which the first catheter passes. The delivery device may include a second catheter adapted to releasably couple with the second attachment feature. The first catheter and the second catheter may be arranged coaxially. The elongate element may be arranged coaxially with the first and second catheters.

In a second general aspect, a method of deploying an implantable medical device within a body comprises providing a medical device delivery system comprising an implantable medical device, a delivery device, and a delivery sheath, configuring the implantable medical device in a delivery configuration within the delivery sheath, advancing a distal end of the delivery sheath to a deployment site within the body, and deploying the implantable medical device. The implantable medical device includes a first attachment feature. The first attachment feature includes an elastomeric element. The delivery device includes a first catheter that is arranged to contact the elastomeric element. The delivery device includes an elongate element that is arranged to releasably couple with the elastomeric element.

In various implementations, the method of deploying an implantable medical device within a body may further comprise retracting the delivery sheath a first distance to expose at least a portion of the implantable medical device, and retracting the first catheter and the elongate element a second distance, wherein the first distance is greater than the second distance. The method may further comprise, after retracting the first catheter and the elongate element a second distance, retracting the elongate element while preventing the first catheter from being substantially retracted, to cause decoupling of the elongate element from the elastomeric element. The implantable medical device may include a second attachment feature, and the delivery device may include a second catheter. The second catheter may be adapted to releasably couple with the second attachment feature, and the first catheter may be arranged to be engaged with the second attachment feature. The method may further comprise removing the first catheter from being in contact with the elastomeric element and disengaging the first catheter from the second attachment feature. Deploying the implantable medical device further may comprise decoupling the second catheter from the second attachment feature. The delivery system may include a deployment actuator coupled to the delivery device and the delivery sheath. The deployment actuator may be adapted to be operated externally of the body by a user. The deployment actuator may be adapted to control positioning of the implantable medical device.

In another general aspect, this document provides another medical device delivery system. The medical device delivery system comprises: an implantable medical device including an attachment feature disposed near a proximal end of the device, wherein the attachment feature includes an elastomeric element that is fixedly attached to the attachment feature, and wherein the elastomeric element includes a channel that extends in an axial direction through the elastomeric element; and a delivery device including a catheter with a distal end that is arranged to abut the elastomeric element, and an elongate element located substantially coaxially within the catheter, wherein the elongate element including a bulbous distal tip that is arranged to releasably couple with the elastomeric element, and wherein the elongate element is adapted to pass through the channel.

In various implementations, the medical device delivery system may further comprise a deployment actuator coupled to the delivery device and to the delivery sheath, and wherein the deployment actuator is adapted to control positioning of the implantable medical device. The medical device delivery system may further comprise a deployment actuator coupled to the delivery device and to the delivery sheath, and the deployment actuator may be adapted to control positioning of the implantable medical device.

In another general aspect, this document provides a method of deploying an implantable medical device within a body. The method comprises: providing a medical device delivery system; configuring the implantable medical device in a delivery configuration within the delivery sheath and advancing a distal end of the delivery sheath to a deployment site within the body; and deploying the implantable medical device. The medical device comprises: an implantable medical device including an attachment feature disposed near a proximal end of the device, wherein the attachment feature includes an elastomeric element that is fixedly attached to the attachment feature, and wherein the elastomeric element includes a channel that extends in an axial direction through the elastomeric element; and a delivery device including a catheter with a distal end that is arranged to abut the elastomeric element, and an elongate element located substantially coaxially within the catheter, wherein the elongate element including a bulbous distal tip that is arranged to releasably couple with the elastomeric element, and wherein the elongate element is adapted to pass through the channel; and a delivery sheath.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIGS. 2A-2J depict example controllable deployment systems and methods for transcatheter deployment of an implantable medical device.

Like reference numbers and designations in the various drawings indicate like elements.

DETAILED DESCRIPTION

This document provides deployment systems and methods that are useful, for example, for controllably deploying implantable medical devices at desired locations, such as within bodily cavities, organs, and vessels. The systems and methods provided herein can be used for transcatheter deployment of implantable medical devices. Various embodiments of implantable medical devices can be configured for containment within a deployment sheath. In some cases the implantable medical device can be collapsed to be contained within a deployment sheath. The collapsed implantable medical device can later be reconfigured to an expanded configuration at or near the implantation site upon deployment from the sheath. The systems and methods provided herein can enable a controllable deployment process, whereby a clinician operator can control the positioning of the implantable medical device in a desired position prior to releasing the device.

Figure 1A:
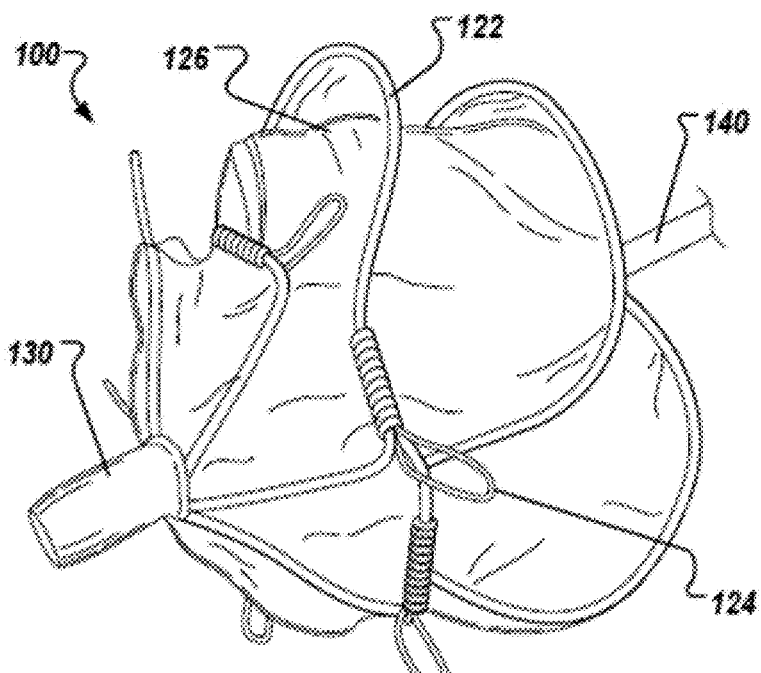
FIGS. 1A and 1B depict an example implantable medical device that can be deployed within a bodily cavity or vessel using the deployment systems and methods provided herein.
Figure 1B:
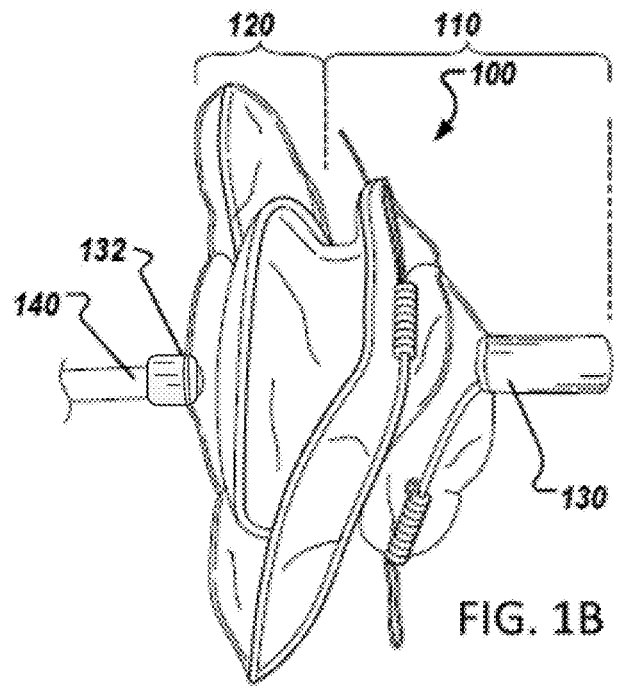

FIGS. 1A and 1B illustrate an example implantable medical device 100 that can be deployed within a bodily cavity or vessel using the deployment systems and methods provided herein. The example implantable medical device 100 can be used to occlude a structure or a conduit, such as an LAA or other aperture within the body. Implantable medical device 100 is provided as an illustrative example in order to describe the deployment systems and methods provided herein, but the deployment systems and methods provided herein can also be used with many other types of implantable medical devices. Further non-limiting examples will be provided below, and many other beneficial applications of the deployment systems and methods provided herein, in conjunction with other types of devices (e.g., vascular implantable medical devices, patent ductus arteriosus (PDA)

implantable medical devices, embolic filters, stent graft devices, electrodes, probes, leads, leadless heart surveillance devices, heart valve frames or stents, shunts, and others) are envisioned. For further information regarding additional examples of medical devices that the deployment systems and methods disclosed herein can be used with, and for example discussions regarding making the devices, see co-pending U.S. patent application Ser. No. 13/615,228 titled, "Occlusive Devices," filed 13 Sep. 2012, with Coby C. Larsen, Steven J. Masters, and Edward E. Shaw as inventors, the entire contents of which are hereby incorporated by reference for all purposes.

In some embodiments, an implantable medical device may include multiple regions or portions. For example, referring to FIGS. 1A and 1B, the example implantable medical device 100 includes a distal portion 110 and a proximal portion 120. The distal portion 110 and the proximal portion 120 can be joined at an inflection region. The example implantable medical device 100 is shown in conjunction with an example delivery device 140. In some embodiments, the delivery device 140 can be releasably coupled to both the distal portion 110 and the proximal portion 120, as will be described further below.

As described above, some implantable medical devices can be configured in a collapsed configuration for containment within a deployment sheath, and then reconfigured to an expanded configuration at the implantation site upon deployment from the sheath. To that end, the example implantable medical device 100 is shown in its deployed or expanded configuration. That is, the example implantable medical device 100 is shown in an expanded configuration similar to the configuration that the example implantable medical device 100 would have at a target deployment site within a bodily cavity or vessel. However, prior to its deployment, the example implantable medical device 100 can be contained within a delivery catheter or sheath, and the example implantable medical device 100 can be in a collapsed configuration so as to fit within the delivery sheath. The systems and methods provided herein can be used to deploy an implantable medical device, such as example implantable medical device 100, from a delivery sheath to a target deployment site within a bodily cavity or vessel in a controllable fashion.

In some embodiments, an implantable medical device is constructed from one or more components and sub-components. For example, the example implantable medical device 100 includes frame members 122, anchors 124, covering 126, distal eyelet 130, and proximal eyelet 132. As used herein, "frame" may refer to an entire frame of a device, or may alternatively refer to a localized portion of a device that includes at least one elongate member. In addition, "frame" refers to various forms of frames, including, but not limited to, tubes, wires, and other suitable types of frames.

An implantable medical device often includes one or more frame members that can provide a structure and shape for the medical device. For example, the example implantable medical device 100 includes frame members 122. Frame members can be one or more elongate elements, such as wire-like elements. Some implantable medical devices may include a single wire-like frame member that is shaped as desired to suit the purpose of the device. In some embodiments, multiple wire-like frame elements may be included in a single implantable medical device. For example, the example implantable medical device 100 includes six frame members 122.

Some embodiments of implantable medical devices include one or more attachment features to which the deployment system can releasably couple. As described further below, in some embodiments the end portions of the one or more frame members are coiled to form eyelets that can serve as attachment features. In some embodiments, eyelets are formed by looping or twisting frame members. Such eyelet attachment features can be used by the deployment system to exert control over the implantable medical device during the deployment process. The control aspects can include, for example, the positioning and release of the implantable medical device.

In some embodiments, the implantable medical device is configured to self-expand when released from the confines of a delivery sheath as a result of a bias or shape-memory property of the frame members. For example, the example implantable medical device 100 is shown in an expanded configuration, which is a result of the self-expanding nature of its frame members 122. Frame members can be, for example, spring wires, shape memory alloy wires, or super-elastic alloy wires. Frame members can be made of nitinol (NiTi), L605 steel, stainless steel, or any other appropriate biocompatible material. The super-elastic properties of NiTi make it a particularly good candidate material for such frame members (e.g., NiTi wires can be heat-set into a desired shape). The frame members may include one or more bend regions that can provide, for example, suitable positions for anchoring features, such as the fixation anchors 124 provided on example medical device 100.

In some embodiments, implantable medical devices include various types of fixation anchors. Fixation anchors can contact surrounding tissue at a target deployment site so as to secure the position of the device, or certain portions of the device, at the target deployment site. For example, the example implantable medical device 100 includes fixation anchors 124 on the distal region 110, but not on the proximal region 120. While in some embodiments of an implantable medical device, fixation anchors can be provided on the proximal region 120 of the device or on multiple regions of the device, in some embodiments no fixation anchors are provided. Fixation anchors can be made from a variety of suitable materials. For example, the fixation anchors can be made of NiTi, L605 steel, stainless steel, a polymeric material, or any other appropriate biocompatible material. In some embodiments, the fixation anchors can be made from a non-permanent biodegradable or bioabsorbable material. The super-elastic properties of NiTi make it a particularly good candidate material for such fixation anchors. NiTi can be heat-set so that a fixation anchor can self-expand into a desired shape when the fixation anchor is placed in a less restrictive environment, such as when it is deployed from the delivery sheath to a body cavity. In some embodiments, it is desirable for a fixation anchor to be biased to have a particular shape to enhance the anchoring properties of the fixation anchor.

Some implantable medical devices can include membranous coverings that, for example, inhibit or prevent passage of blood and other bodily fluids. For example, the example implantable medical device 100 includes covering 126. In some embodiments, covering 126 is a thin flexible material. In some embodiments, the covering has a microporous structure that provides a tissue ingrowth scaffold for durable occlusion and supplemental anchoring strength of the implantable medical device. In some embodiments, the covering comprises a fluoropolymer, such as an expanded polytetrafluoroethylene (ePTFE) polymer.

In some embodiments, the implantable medical device includes various types of attachment features. Such attachment features can provide a location for the releasable coupling of deployment systems to the implantable medical device. For example, some implantable medical devices include one or more attachment hubs for the attachment of deployment systems. In some embodiments, the hubs include, for example, a threaded hole. A deployment device may include a corresponding threaded feature to enable releasable coupling between the hub of the implantable device and the deployment device. In some embodiments, the attachment features are releasably keyed or pinned to a deployment device.

The example implantable medical device 100 has attachment features that include two eyelets, i.e., distal eyelet 130 and proximal eyelet 132. Other implantable medical device embodiments may include a single attachment feature (e.g., a single eyelet or a single hub). In some such embodiments, the single attachment feature is located near the proximal end of the device. In some such embodiments, the single attachment feature is located near the distal end of the device. In some such embodiments, the single attachment feature is located between the proximal and distal ends of the device. The distal eyelet 130 and proximal eyelet 132 can be made from the coiled end portions of the one or more frame members 122. In some embodiments, the distal eyelet 130 and proximal eyelet 132 can be covered with the covering 126. As will be described further in reference to FIGS. 2A-2J, some eyelets can be inverted eyelets. For example, inverted eyelets are coiled frame members that are positioned within the interior of the space defined by the frame elements of the medical device. In contrast, distal eyelet 130 is not an inverted eyelet since it is positioned outside of the space defined by the frame members 122 of the distal portion 110.

In reference to FIGS. 2A-2J, a series of deployment system configurations and actions for controllably deploying an implantable medical device using the provided systems and methods for minimally invasive transcatheter device deployment are depicted. In general, the actions include: attaching a deployment device to an implantable medical device, configuring the implantable medical device within a delivery sheath, advancing the delivery sheath through a patient's vasculature and positioning a distal end of the delivery sheath at a target in vivo deployment site, deploying the medical device, confirming that the medical device is positioned as desired or, if not positioned as desired, repositioning the medical device, releasing the medical device from the deployment system, and retracting the deployment system from the body.

Figure 2A:
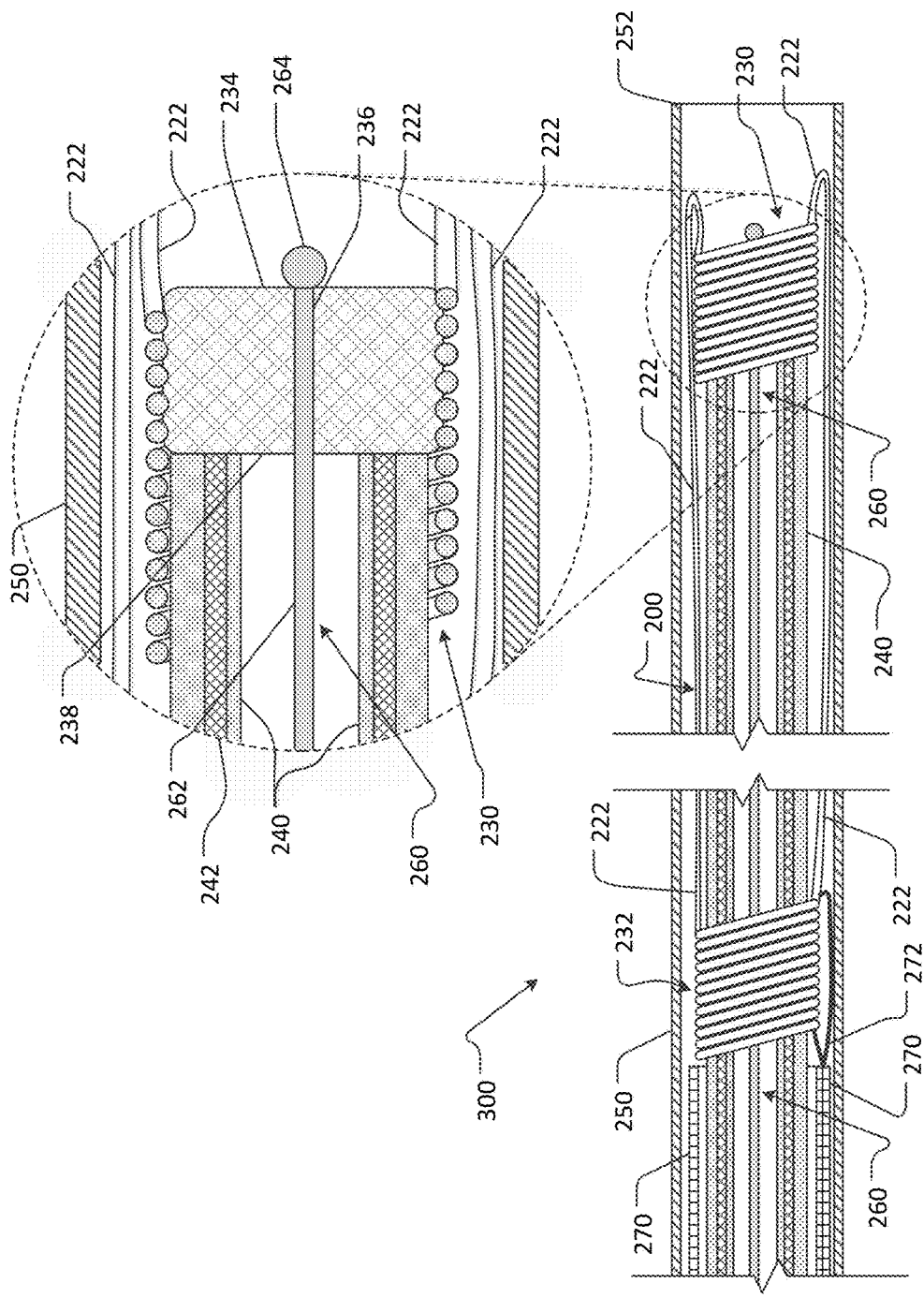

FIG. 2A depicts, in the primary view on the bottom of the figure, an axial cross-section of a distal portion of a controllable implantable medical device deployment system 300. A proximal portion of the controllable implantable medical device deployment system 300 is not shown. The proximal portion can include an operator interface in the form of a deployment actuator. The deployment actuator can be connected to the proximal ends of components of the controllable implantable medical device deployment system 300 described herein. The deployment actuator can be used by a clinician operator to actuate the various movements of the distal portion of the controllable implantable medical device deployment system 300 that are described in reference to FIGS. 2A-2J and FIGS. 3A-3B.

In general, a deployment system 300 can include an implantable medical device within a delivery sheath. For example, in FIG. 2A the deployment system 300 includes example implantable medical device 200 that is in a collapsed configuration contained inside of delivery sheath 250. The delivery sheath 250 is shown in cross-section to enable better visualization of the collapsed implantable medical device 200 and the other deployment system components (as described below) located within the delivery sheath 250. An open distal end 252 of the delivery sheath is located on the right side of the figure. A distal end of the implantable medical device 200 (near distal eyelet 230) is shown in an enlarged view to provide additional detail of the distal end of the medical device and its relation with certain components of the deployment system 300.

The delivery sheath 250 can be, for example, a tube that is used to constrain an implantable medical device, and to percutaneously deliver the implantable medical device to a target deployment site within a bodily cavity or vessel. The tubular delivery sheath 250 can have a circular cross-section or another cross-sectional shape, such as ovular or other suitable shapes. A proximal end of the delivery sheath 250 can be attached to a deployment actuator (e.g., a handheld deployment actuator or a non-handheld deployment actuator) that can be operated by a clinician operator. In some embodiments, the deployment actuator may provide one or more controls that permit a clinical operator to control one or more aspects of the delivery sheath 250. In some embodiments, the delivery sheath 250 can be a steerable delivery sheath. In some embodiments, at least the distal end 252 portion of the delivery sheath 250 can be steerable. In some embodiments, a guidewire may be installed in the patient first, and the delivery sheath 250 may be installed over the guidewire. The delivery sheath 250 can have one lumen or multiple (e.g., two or more) lumens. A lumen of the delivery sheath 250 can contain an implantable medical device, and in some embodiments the implantable medical device is configured in a collapsed configuration.

Delivery sheath 250 contains an example implantable medical device 200. In some embodiments, the example implantable medical device 200 is an occluder device that is similar to the example medical device 100 shown in FIGS. 1A and 1B. However, the systems and methods provided herein for controllably implanting a medical device can be used with a variety of types of implantable medical devices in addition to occluder devices. The occluder device 200 is merely provided as an example of one type of device that can be deployed using the deployment systems and methods provided herein.

Certain components of implantable medical device 200 can be identified in FIG. 2A that substantially correspond to those defined above in reference to FIGS. 1A and 1B. For example, wire-like frame members 222 are shown in a collapsed configuration within the sheath 250. Distal eyelet 230 is shown in both the primary axial cross-sectional view and the enlarged view. The distal eyelet 230 in the enlarged view is shown in cross-section to enable better visualization of the components located within a space defined by the distal eyelet 230. The proximal eyelet 232 is shown in the primary view. The example implantable medical device 200 may also include a variety of other features and components, such as a membranous covering, fixation anchors, or combinations and sub-combinations thereof, and so on, but for clarity such additional features and components are not shown in the schematic figures (FIGS. 2A-2J).

The distal and proximal eyelets 230 and 232 of the medical device 200 are visible in detail in FIG. 2A. As described above, the distal and proximal eyelets 230 and 232 can, in some embodiments, be formed from the coiled end portions of frame members 222, such as shown here. For clarity, the extended lengths of only two frame members 222 are shown in FIG. 2A. In some embodiments, the distal and proximal eyelets 230 and 232 can be used as attachment features, i.e., portions of the medical device to which a deployment system can releasably couple for deploying and positioning the implantable medical device. The distal and proximal eyelets 230 and 232 are an example of one type of attachment feature. As mentioned above, other types of attachment features can also be utilized with the controllable deployment system and methods provided herein—such as hubs, for example (refer to FIG. 4). Further, some embodiments of implantable medical devices may have more than, or fewer than, two attachment features. Such embodiments of medical devices can also be controllably deployed using the systems and methods provided herein.

The distal and proximal eyelets 230 and 232 are the coiled terminations of the wire-like frame members 222. Therefore, controlling the distal and proximal eyelets 230 and 232 provides a way to physically control the frame members 222, and to thereby physically control the implantable medical device 200 overall. As described further below, the controllable implantable medical device deployment system 300 can control an implantable medical device via the attachment features of the device, e.g., distal and proximal eyelets 230 and 232 of implantable medical device 200, to provide a clinician operator with control over the in vivo positioning of an implantable medical device.

One or more attachment features of an implantable medical device can include an elastomeric element. As used herein, the term "elastomeric" used in the context of a material or an object, means that the material or object is at least partially deformable, and that the material or object may recover at least partially to its pre-deformed shape to varying degrees. The elastomeric element can be used advantageously for releasably coupling components of the deployment system to the attachment feature. That is, the elastomeric element of the attachment feature can enable control of the attachment feature via the coupling of the medical device to the deployment system, and can facilitate the de-coupling of the deployment system from the attachment feature by elastically deforming the elastomeric element when the clinician operator desires to decouple the deployment system from the medical device.

For example, the distal eyelet 230 of the example implantable medical device 200 can include a elastomeric element 234 (see enlarged view). In some embodiments, the elastomeric element can be fixedly coupled to the attachment feature, e.g., elastomeric element 234 can be fixedly coupled to distal eyelet 230. That is, the elastomeric element can remain permanently coupled to the medical device after the release of the medical device from the deployment system. In that arrangement, the elastomeric element can remain implanted in the patient as an integral component of the medical device. In some embodiments, the elastomeric element can be fixedly coupled to the delivery device, and releasably coupled to the attachment feature of the implantable medical device.

In some embodiments, the elastomeric element comprises a biocompatible resilient polymeric material that is capable of being elastically deformable. As one example, the elastomeric element can include a fluorinated ethylene propylene (FEP) material. In some embodiments, the elastomeric element can comprise silicone, and other suitable flexible biocompatible materials. In some embodiments, the elastomeric element comprises a bioresorbable material.

In some embodiments, a mechanical device is used as the elastomeric element. For example, the elastomeric element can include spring loaded portions that can be elastically deflected. In some embodiments, a mechanical elastomeric element device includes an arrangement of one or more tabs that can be elastically deflected (refer to FIG. 4). In some embodiments, the elastomeric element comprises a combination of polymeric and mechanical portions.

In some embodiments, the elastomeric element is a plug that is assembled to the attachment feature. For example, the elastomeric element can include a resilient material, e.g., FEP, which is contained within or surrounded by a jacket or sleeve to form a plug. The jacket material can comprise a variety of biocompatible materials, including polymeric or metallic materials. The jacketed resilient material (plug) can be coupled with an attachment feature. For example, in some cases the plug can be press fit into an opening on the attachment feature. In some embodiments, the plug is adhered to the attachment feature using an adhesive or by welding.

The example implantable medical device 200 includes an elastomeric element 234 that is fixedly coupled to distal eyelet 230. In this example, elastomeric element 234 is a polymeric material, such as FEP, and no jacket is included, i.e., it is not a plug. The elastomeric element 234 is fixedly engaged with the coils of the distal eyelet 230. In some embodiments, the elastomeric element 234 can be press-fit into the distal eyelet, and remains in place by a friction fit. In some embodiments, the elastomeric element 234 is adhered to the distal eyelet using a suitable biocompatible adhesive. In some embodiments, the elastomeric element 234 in a liquid state can be poured or potted in the distal eyelet 230, and allowed to later solidify and cure.

An elastomeric element, in addition to being coupled to an attachment feature of a medical device, can be coupled to one or more components of a deployment system. The coupling between the elastomeric element and the components of the deployment system can include releasable or fixed couplings. In some embodiments, the deployment system can compress the elastomeric element to enlarge a portion of the elastomeric element, such as an outer periphery, which can thereby engage with an attachment feature on a medical device. In some embodiments, the elastomeric element can be fixed to the deployment system and the attachment feature can include a component with a bulbous tip that can engage with the elastomeric element. The coupling between the elastomeric element and the deployment system can provide the ability for the clinician operator to manipulate the deployment system to thereby exert control over the medical device.

Various coupling arrangements between the elastomeric element and the deployment system, in addition to the example provided in FIG. 2A, are envisioned. In some embodiments, the attachment features are releasably keyed or pinned to a deployment device. In some embodiments, the deployment system includes a wire with a helical tip end that couples with a corresponding hole in the elastomeric element, such that the deployment system can be unscrewed from the elastomeric element to decouple them. In some embodiments, the attachment feature includes a tube with a slit running lengthwise through a wall of the tube, and the deployment system includes a feature that frictionally engages with the inside of the tube. In such an arrangement, the tube can act as an elastomeric element in that it can provide an extent of resistance to the removal of the engaged deployment system feature, but such resistance can be overcome at the time decoupling is desired.

In some embodiments, the delivery system includes an inner catheter 240 and an inner wire 260. The elastomeric element 234 may interface with inner catheter 240 and inner wire 260. The inner catheter 240 and inner wire 260 can extend proximally from the elastomeric element 234 all the way to the deployment actuator that is operable by a clinician operator for controlling the implantable medical device.

Inner wire 260 can include an elongate element 262 and a distally located bulbous tip 264. In some embodiments, the inner wire 260 can comprise NiTi, L605 steel, stainless steel, a polymeric material, or any other appropriate biocompatible material or combination of such materials. In some embodiments, the elongate element 262 can be a braided construction, or a solid construction, or a combination of both. In some embodiments, as described further below in reference to FIG. 2H, the inner wire 260 includes a bent portion near the distal end of the elongate element 262. The bulbous tip 264 can comprise the same or a dissimilar material as the elongate element 262. In some embodiments, the bulbous tip 264 is a substantially rigid structure. In some embodiments, the bulbous tip 264 is an elastomeric or deformable structure, e.g., the bulbous tip can be made from an elastomeric material such as silicone. In some embodiments, the bulbous tip 264 is an inflatable balloon-like member that can be collapsed to decrease the profile of the bulbous tip 264. In some embodiments, the bulbous tip 264 is mechanically collapsible to thereby decrease the profile of the bulbous tip 264. The bulbous tip 264 can be attached to the elongate element 262 by laser welding, gluing, threading, press-fitting, and the like. In some embodiments, the bulbous tip 264 is formed integrally with the elongate element 262. The bulbous tip 264 can be spherical, ovular, helical, cylindrical, a cube, a rectangular cube, or another suitable shape.

Elastomeric element 234 includes an axially extending tunnel-like through-hole 236 that can releasably receive elongate element 262. The bulbous tip 264 can be located on the distal side of the elastomeric element 234 when the deployment system 300 is coupled to the distal eyelet 230. As described further below, to decouple the deployment system 300 from the elastomeric element 234, the bulbous tip 264 can be pulled through the axial through-hole 236 of the elastomeric element 234 to elastically deform the elastomeric element 234 when the clinician operator pulls the inner wire 260. In some embodiments, an application of a proximally directed force on inner wire 260 while holding the inner catheter 240 stationary is provided. Inner wire 260 extends through a lumen of an inner catheter 240. The proximal end of the inner wire 260 can be coupled to the deployment actuator, and the deployment actuator may provide one or more controls that permit a clinical operator to control one or more aspects of the inner wire 260.

In some embodiments, inner catheter 240 is a laterally-flexible polymeric tubular component of the deployment system 300. The proximal end of the inner catheter 240 can be coupled to the deployment actuator, and the deployment actuator may provide one or more controls that permit a clinical operator to control one or more aspects of the inner catheter 240, e.g., axial extension and holding force. The distal end of the inner catheter 240 can abut a proximal side face 238 of the elastomeric element 234 (see enlarged view). In some embodiments, the delivery system 300 also includes an outer catheter 270, and the inner catheter 240 can be routed through the outer catheter 270, as depicted in FIG. 2A.

The inner catheter 240 can also be routed through one or more attachment features of the medical device, such as the proximal eyelet 232 and a portion of the distal eyelet 230. In some embodiments, the distal end of the inner catheter 240 can be located within a proximal portion of the distal eyelet 230 (see enlarged view). In some embodiments, the engagement between the outer periphery of the inner catheter 240 and the inner periphery of the eyelets 230 and 232 is a slip fit. When the inner catheter 240 is engaged with the proximal eyelet 232 and the distal eyelet 230, for example, the inner catheter 240 can provide support to the medical device 200 and can be used to control the locations of the eyelets 230 and 232 and thereby substantially control the position of the medical device overall.

In some embodiments, the cross-sectional shape of the inner catheter 240 is circular. In some embodiments, the cross-sectional shape of the inner catheter 240 is non-circular. For example, in some embodiments, the inner catheter 240 can have an ovular, square, rectangular, or another suitable cross-sectional shape. In some embodiments, the inner shape of the attachment features that engage with the inner catheter 240 have shapes corresponding to the shape of the inner catheter 240. For example, if the inner catheter 240 has an ovular cross-sectional shape, the eyelets 230 and 232 can have a corresponding ovular interior shapes. As such, the eyelets 230 and 232 may be "keyed" to the inner catheter 240. In such a keyed arrangement, the eyelets 230 and 232 can be prevented from rotating in relation to the inner catheter 240. In some embodiments, a keyed arrangement can also facilitate an application of torque to the eyelets 230 and 232 from the inner catheter 240. Such an arrangement can, in some embodiments, be advantageously used to provide an additional extent of control over the medical device by the deployment system.

In some embodiments, the inner catheter 240 includes a reinforcement layer 242 to increase the compressive rigidity or column strength of the inner catheter 240. In some embodiments, the reinforcement layer 242 is embedded in the wall of the inner catheter 240 as shown. For example, the inner catheter can be molded, extruded, or formed around the reinforcement layer 242. In some embodiments, the reinforcement layer 242 is attached to a surface of the inner catheter 240. For example, the reinforcement layer 242 can be adhered to the inner surface, or the outer surface, or both the inner and the outer surfaces of the inner catheter 240. In some embodiments, the reinforcement layer 242 comprises a braided mesh of metallic material such as a stainless steel material or other suitable material. In some embodiments, the reinforcement layer 242 comprises a closed-coiled metallic material similar to an extension spring. In some embodiments, the reinforcement layer 242 comprises a plurality of single wire strands that run generally parallel with the longitudinal axis of the inner catheter 240.

As will be described further below (in reference to FIG. 2G), the reinforcement layer 242 of the inner catheter 240 can provide additional column strength, to resist compressive deflection of the inner catheter 240 from the compressive forces exerted by the elastomeric element 234 when the bulbous tip 264 of the inner wire 260 is pulled through the elastomeric element 234. In some embodiments, the inner catheter 240 does not include a reinforcement layer 242.

The elastomeric element 234 can be arranged between the bulbous tip 264 of the inner wire 260 and the distal end of the inner catheter 240. In this arrangement, a clinician operator can control the position of the elastomeric element 234 (and consequently the distal eyelet 230) by manipulating the position of the inner wire 260 and inner catheter 240. That is, by pushing or pulling the inner catheter 240 and the inner wire 260 in combination (or in some cases one or the other), such movements can induce corresponding movements of the elastomeric element 234, the distal eyelet 230, and the frame elements 222 that are attached to the distal eyelet 230. In addition, torque or twisting forces can be exerted on the elastomeric element 234 and distal eyelet 230 by twisting the combination of the inner catheter 240 and the inner wire 260. In some embodiments, non-circular inner shapes of the attachment features engage with complimentary non-circular inner catheter 240 shapes to facilitate the application of such torque or twisting forces.

In some embodiments, the inner catheter 240 is located within a lumen of an outer catheter 270. Outer catheter 270 is best visible on the left side of the primary view of FIG. 2A. Outer catheter 270 is shown in axial cross-section to allow viewing of the components within the lumen of the outer catheter 270. In some embodiments, the outer catheter 270 has a proximal end attached to a deployment actuator of the deployment system, and a distal end of the outer catheter is located near an attachment feature of the implantable medical device (e.g., proximal eyelet 232) within a delivery sheath of the deployment system. In some embodiments, the deployment actuator provides one or more controls that permit a clinical operator to control one or more aspects of the outer catheter 270. In some embodiments, outer catheter 270 includes a primary lumen that contains inner catheter 240.

In some embodiments, outer catheter 270 also includes two or more lumens through which a suture tether 272 may pass. In some embodiments, the suture tether 272 is a strand of suture material that is used to couple the outer catheter 270 to an attachment feature of the medical device by tethering them together. For example, as illustrated by the example deployment system 300, the outer catheter 270 can be coupled to the proximal eyelet 232 using the suture tether 272. In some embodiments, the suture tether 272 is a single length of suture material with both ends of the suture tether 272 located at the proximal end of the deployment system, such as near or at the deployment actuator of the deployment system. In some embodiments, the suture tether 272 is routed from the proximal end of the deployment system, through a first small lumen in the outer catheter 270, exiting the first lumen at the distal end of the outer catheter 270, coupling to an attachment feature of the medical device (e.g., proximal eyelet 232), entering a second small lumen at the distal end of the outer catheter 270, and running back through the second lumen to the proximal end of the deployment system. The clinician operator can tug on the ends of the suture tether 272 to snug the outer catheter 270 to the attachment feature. In some embodiments, the clinician operator can clamp the ends of the suture tether 272 to secure the coupling of the outer catheter 270 to the attachment feature of the medical device. When the outer catheter 270 is snugged to the attachment feature, movement of the outer catheter 270 will induce corresponding movement of the attachment feature and other portions of the medical device that are connected to the attachment feature. In the example provided, the outer catheter 270 and the suture tether 272 are coupled to and control the movement of the proximal eyelet 232 of the example medical device 200. In some embodiments, one or both ends of the suture tether 272 may be coupled to the deployment actuator, which may provide one or more controls that may permit the clinical operator to control one or more aspects of the suture tether 272.

The deployment system 300 with the example medical device 200 as shown in FIG. 2A represents the configuration that the deployment system 300 containing the example medical device 200 would be in as delivered to a target deployment site within a bodily cavity or vessel. That is, the configuration shown would be the configuration that the deployment system 300 and device 200 would be in when they are routed within the bodily cavity or vessel to the site where the device 200 is to be implanted.

FIGS. 2B-2J illustrate various example configurations that the deployment system may be in, and various techniques that may be used, during the process of deploying a medical device using the systems and methods provided herein for controllably deploying a medical device.

Figure 2B:
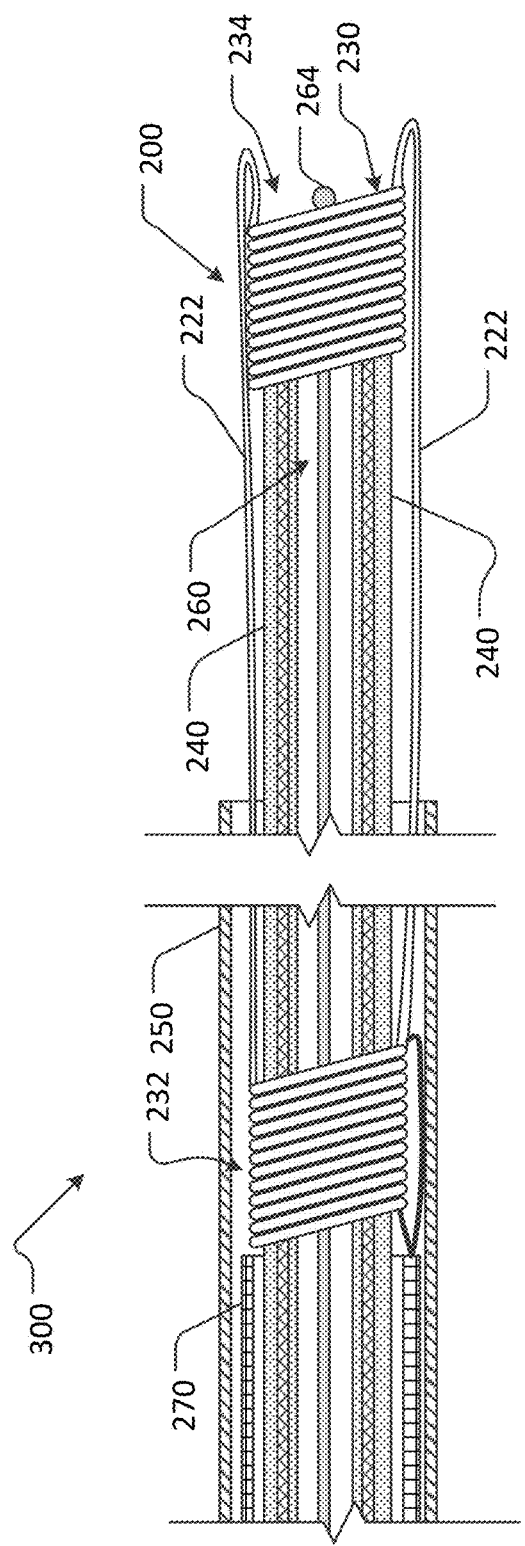

With reference first to FIG. 2B, the deployment system 300 is shown with the delivery sheath 250 in a partially retracted position such that a distal portion of the medical device 200 is exposed. This configuration can be attained in accordance with the actions of a clinician operator who operates a deployment actuator of the deployment system 300. For example, the operator may operate a control of the deployment actuator that causes the delivery sheath 250 to retract or be pulled back in a proximal direction. The difference between the configuration of FIG. 2B and the configuration of FIG. 2A is that the delivery sheath 250 has been retracted by a distance so as to expose a distal portion of the medical device 200. In some embodiments, tactile feedback is provided to indicate that the delivery sheath 250 has been retracted by an appropriate distance. The other components of the deployment system 300 have been generally maintained in their prior positions. For example, the locations of the inner catheter 240 and inner wire 260, generally, have not changed.

Because the locations of the inner catheter 240 and inner wire 260, in general, have not been changed, the example medical device 200 is still in a collapsed configuration. That is, in this configuration, the medical device 200 remains in a collapsed state because the medical device 200 is being held in tension (for example, based on the positions of the distal and proximal eyelets). In other words, the frame elements 222 of the medical device 200 do not self-expand because the medical device 200 is being held in tension between the distal eyelet 230 and the proximal eyelet 232. In particular, the tension between the distal eyelet 230 and the proximal eyelet 232 is created and maintained because: (i) the inner catheter 240 prevents the distal eyelet 232 from moving substantially proximally; and (ii) the outer catheter 270 prevents (e.g., in conjunction with the suture tether 272) the proximal eyelet 232 from moving substantially distally.

Figure 2C:
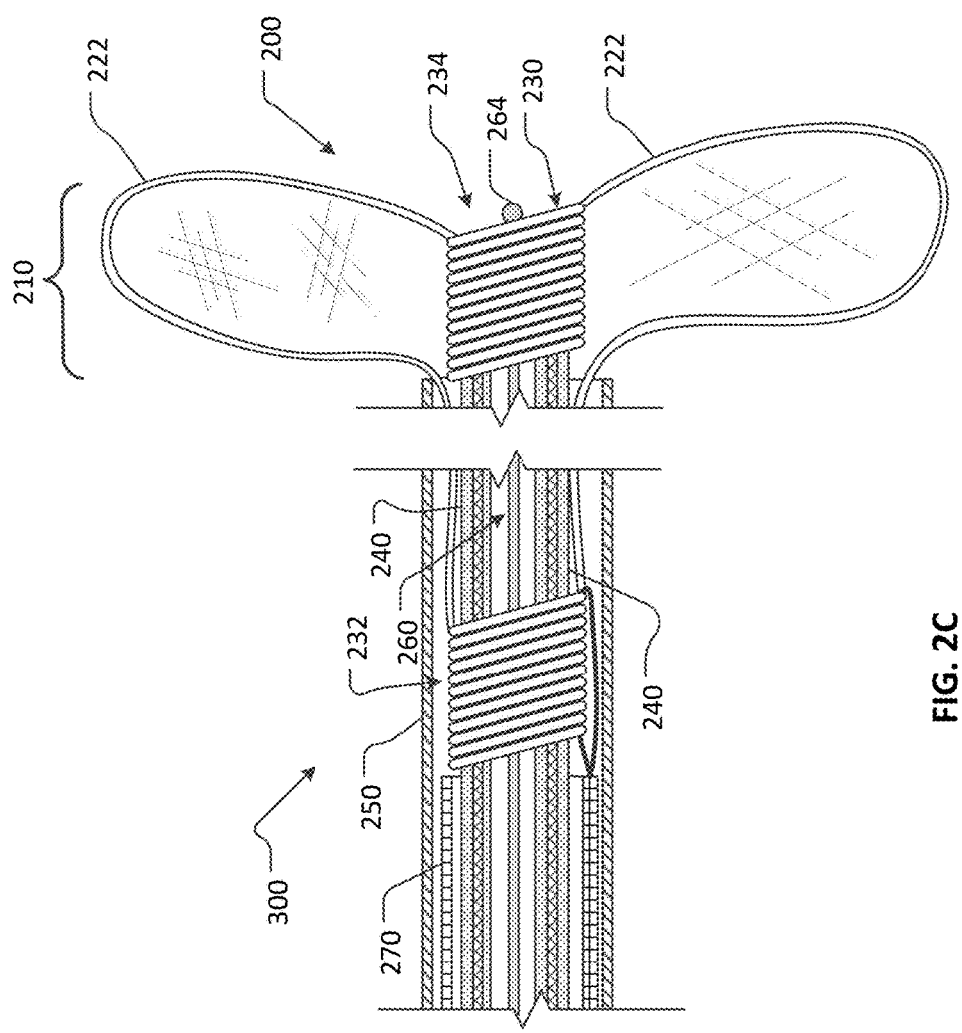

In reference to FIG. 2C, the deployment system 300 is shown with the inner catheter 240 and the inner wire 260 having been retracted from their previous locations depicted in FIG. 2B. That is, the tension that previously existed between the distal eyelet 230 and the proximal eyelet 232 has been partially relieved based on the retraction or proximal movement of the distal eyelet 230. The partial removal of the tension can allow portions of the frame elements 222 of the distal portion 210 of the medical device 200 to at least partially self-expand.

To arrive at the configuration of FIG. 2C, in some embodiments the clinician operator may retract the inner catheter 240 and the inner wire 260 simultaneously. As described in reference to FIG. 2A, the elastomeric element 234 located in the distal eyelet 230 is initially contained between the distal end of the inner catheter 240 and the bulbous tip 264 of the inner wire 260. Therefore, as the clinician operator simultaneously retracts the inner catheter 240 and the inner wire 260, the elastomeric element 234 is also retracted by the same distance as the inner catheter 240 and the inner wire 260. The proximal eyelet 232, however, is not moved by the retraction of the inner catheter and the inner wire. The location of the proximal eyelet 232 is controlled by the location of the outer catheter 270. Since at this stage the outer catheter 270 remains substantially stationary, and the inner catheter 240 and inner wire 260 are retracted, the distal eyelet 230 will thereby move closer to the proximal eyelet 232. As the distance between eyelets 230 and 232 is reduced, some of the tension on the frame elements 222 is relieved, and therefore the frame elements 222 are allowed to self-expand by an amount generally relating to the decrease in distance between the eyelets 230 and 232. Because the portions of the frame elements 222 in the distal portion 210 are no longer contained by the delivery sheath 250, those portions of the frame elements 222 can self-expand (subject to any confinement provided by body tissue at the deployment site), while the more proximal portions of the frame elements 222 that remain within the delivery sheath 250 are presently restrained from expanding.

At this point of the deployment process, the clinician operator can confirm the desirability of the position of the distal portion 210 of the medical device 200 in relation to the surrounding bodily tissue. In general, the clinician may be interested in one or more of the position, location, orientation, anchoring strength, and the sealing properties of the distal portion 210 of the medical device 200 in relation to the surrounding tissue. In some embodiments, radiopaque markers or jackets can be included on the medical device 200, such as, for example, on the frame elements 222 and/or on one or both of the eyelets 230 and 232. In some embodiments, the frame elements 222 comprise a core material that is highly visible using imaging systems. In some cases, clinicians may use magnetic resonance imaging (MRI) or x-ray imaging to visualize the positioning of the distal portion 210.

The clinician operator may also gently tug on the inner catheter 240 and the inner wire 260 simultaneously, or may manipulate the inner catheter 240 and inner wire 260 in various other manners. In some embodiments, the force to pull the bulbous tip 264 into the through-hole 236 can be established at a high enough level of force to allow the clinician operator to tug on the inner catheter 240 without pulling the bulbous tip 264 into the through-hole. The tugging action can serve to seat or embed the anchoring devices on the medical device, if the medical device includes anchoring devices, to tissue at the deployment site.

The tugging action by the clinician operator can also provide the clinician operator with an indication of how securely the medical device is anchored in its position relative to the surrounding bodily tissue. That is, based on the tactile feel in response to a tugging action, a clinician can get an indication of how strongly the medical device is anchored to the surrounding tissue.

If the clinician is dissatisfied with the position or anchorage strength of the distal portion 210 of the medical device 200, the clinician can manipulate the inner catheter 240 and inner wire 260 to reposition the distal portion 210 of the device. After repositioning, the clinician can repeat the process above to confirm the desirability of the position and anchorage of the distal portion 210, in relation to the surrounding tissue, until the clinician is satisfied with the position and anchorage strength.

Figure 2D:
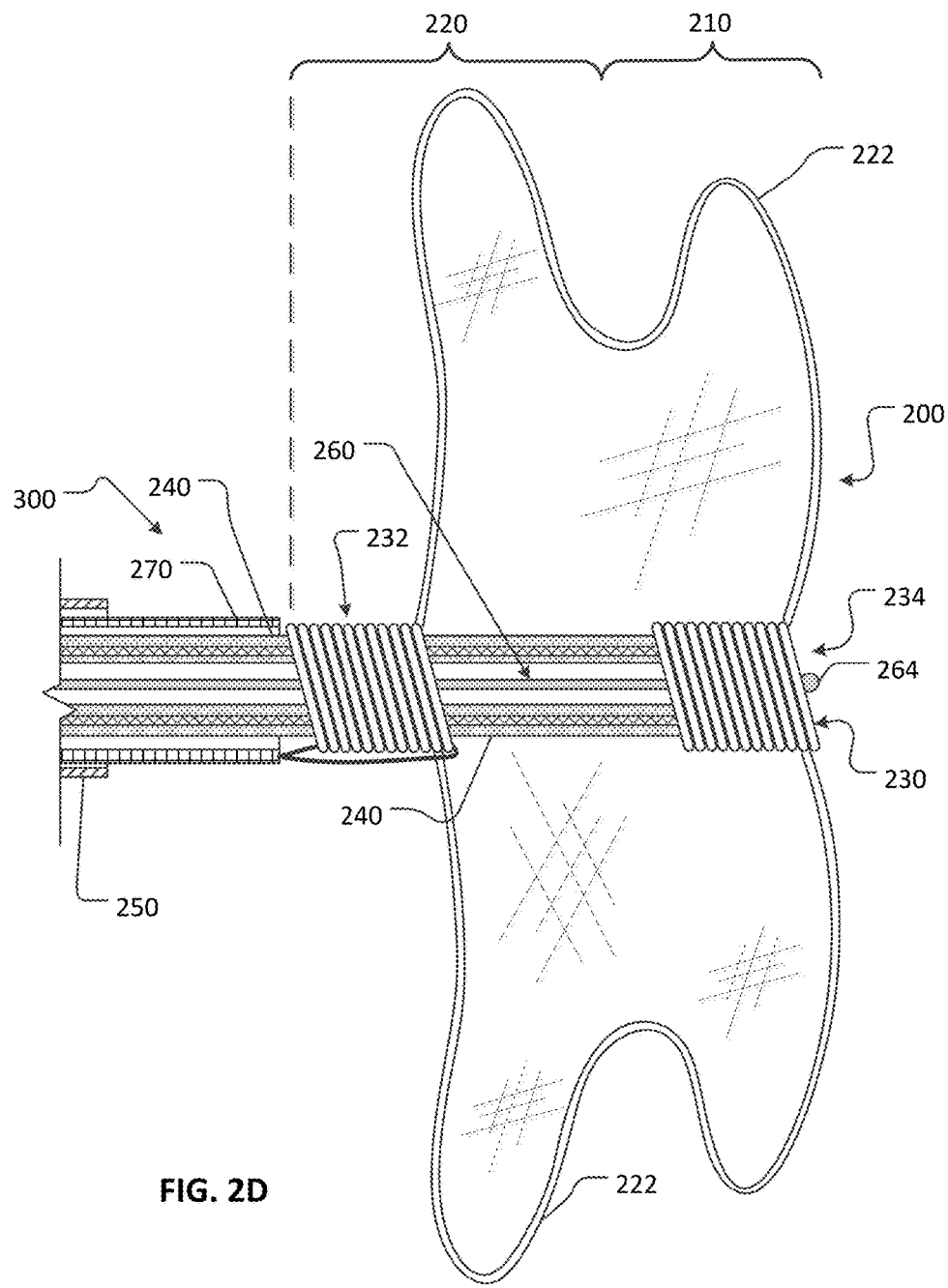

In reference to FIG. 2D, the medical device 200 is shown as having been fully liberated from within the delivery sheath 250, i.e., the delivery sheath 250 has now been fully retracted from the prior position at which it partially constrained the medical device 200. In addition, the eyelets 230 and 232 have been positioned in a spatial relation to each other generally according to their natural spacing as defined by the design of the medical device 200. The spacing between the eyelets 230 and 232 is now such that the frame elements 222 have been allowed to fully expand in accordance with the design of the medical device 200.

To arrive at this configuration, two things have changed from the previous configuration as depicted in FIG. 2C. First, as set forth above, the delivery sheath 250 has been retracted to fully expose all portions of the medical device 200 from the interior of the delivery sheath 250. Second, the inner catheter 240 and inner wire 260 have been retracted or moved proximally to bring the distal eyelet 230 closer to the proximal eyelet 232, such that the eyelets 230 and 232 are generally at their natural positions in relation to each other. Such actions allow the proximal portion 220 of the medical device 200 to expand as shown. For clarity, the distance between the two eyelets 230 and 232 is exaggerated in FIG. 2D as compared to an actual spacing between the two eyelets with some embodiments of the device 200.

At this juncture, the clinician can now assess the desirability of the position of the proximal portion 220 of the medical device 200 in relation to the surrounding tissue. This assessment can use substantially the same techniques described above regarding the confirmation of the positioning and anchorage strength of the distal portion 210. In some embodiments, the clinician can use one or both of the outer catheter 270 and the inner catheter 240, to manipulate the position of the proximal eyelet 232 to reposition the proximal portion 220 of the medical device 200.

Figure 2E:
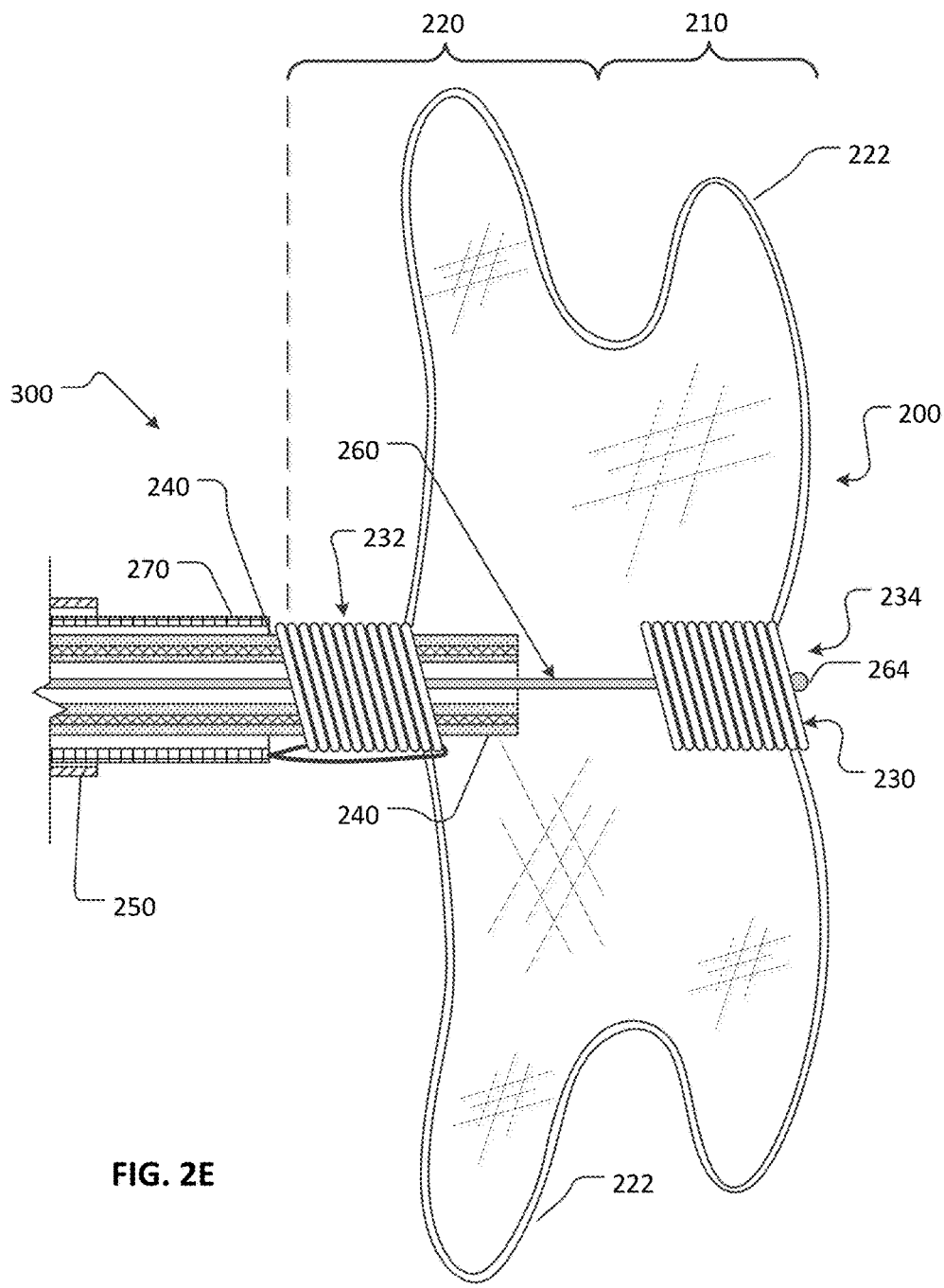

In reference to FIG. 2E, the medical device 200 is shown with the inner catheter 240 of the deployment system 300 temporarily disengaged from the distal eyelet 230. That is, the configuration shown is the same as the previous configuration of FIG. 2D except that the inner catheter 240 has been retracted or moved proximally to disengage from the distal eyelet 230.

In some embodiments, the inner catheter 240 is temporarily disengaged from the distal eyelet 230 to remove any positioning influence that the inner catheter 240 may exert on the distal eyelet 230. When the inner catheter 240 is engaged with the distal eyelet 230, the rigidity of the inner catheter 240 may inhibit the distal portion 210 from assuming the position that it will assume when the inner catheter 240 is removed from the medical device 200. Temporarily removing the inner catheter 240 from the distal eyelet 230 can reduce or eliminate the positional influence that the inner catheter 240 may be exerting on the distal portion 210 and therefore permit a better assessment of device position and orientation at the deployment site. With the inner catheter 240 so removed from the distal eyelet 230, the clinician can visualize the positioning of the distal portion 210 in relation to surrounding tissue using MRI, x-ray, or other visualization techniques. In this configuration, with the inner catheter 240 removed from the distal eyelet, the clinician may obtain a better indication of what the final position of the distal portion 210 of the device will be after the deployment system 300 is removed.

If the clinician is dissatisfied with the positioning of the distal portion 210, or of the device in general, the clinician can re-engage the inner catheter 240 with the distal eyelet 230, for example by distally advancing the inner catheter 240. With the inner catheter 240 re-engaged with the distal eyelet 230, the clinician can exert control over the distal eyelet 230 to reposition the distal portion 210 as desired. The process of disengaging the inner catheter 240 and assessing the positioning of the distal portion 210 can be repeated one or more times until a satisfactory positioning of the distal portion 210 in relation to the surrounding tissue is achieved.

In some embodiments, the outer periphery of the distal tip of the inner catheter includes one or more features that facilitate the re-engagement of the inner catheter 240 with the distal eyelet 230. For example, the outer periphery of the distal end of the inner catheter can include a chamfered or a radiused leading edge (not shown). Such features can function as a "lead-in" feature that can assist with re-engagement of the inner catheter 240 with the distal eyelet 230 despite some potential degree of axial misalignment between them. In some examples, the proximal portion of the distal eyelet may include a "lead-in" feature that assists with re-engagement of the distal eyelet and the inner catheter, and in some examples both the inner catheter and the distal eyelet may include such features.

Figure 2F:
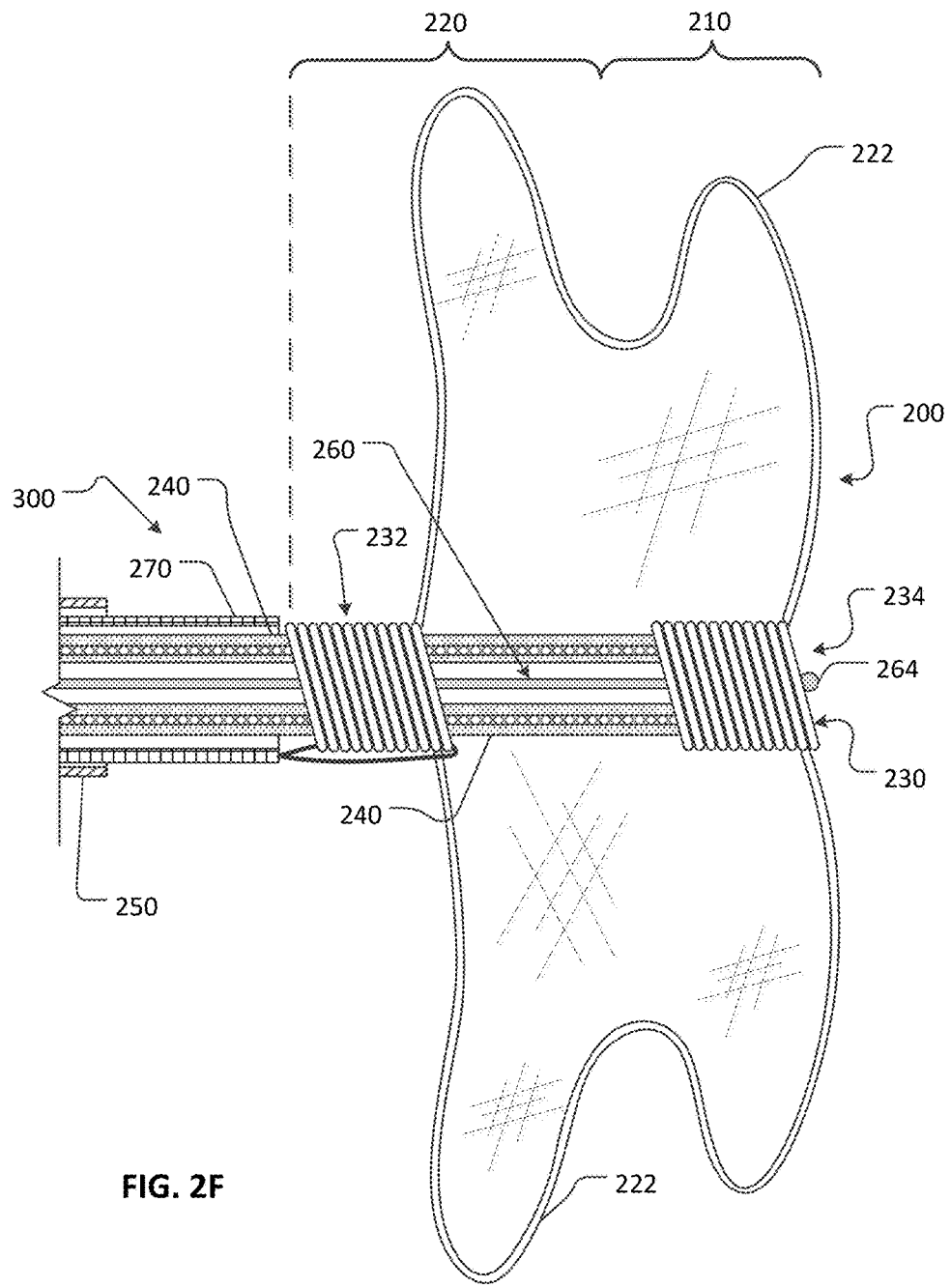

When the clinician is satisfied with the positioning of the distal portion 210, the clinician can re-engage the inner catheter 240 with the distal eyelet 230 in preparation for the removal of the inner wire 260 from the elastomeric element 234. This re-engaged configuration is depicted in FIG. 2F.

Figure 2G:
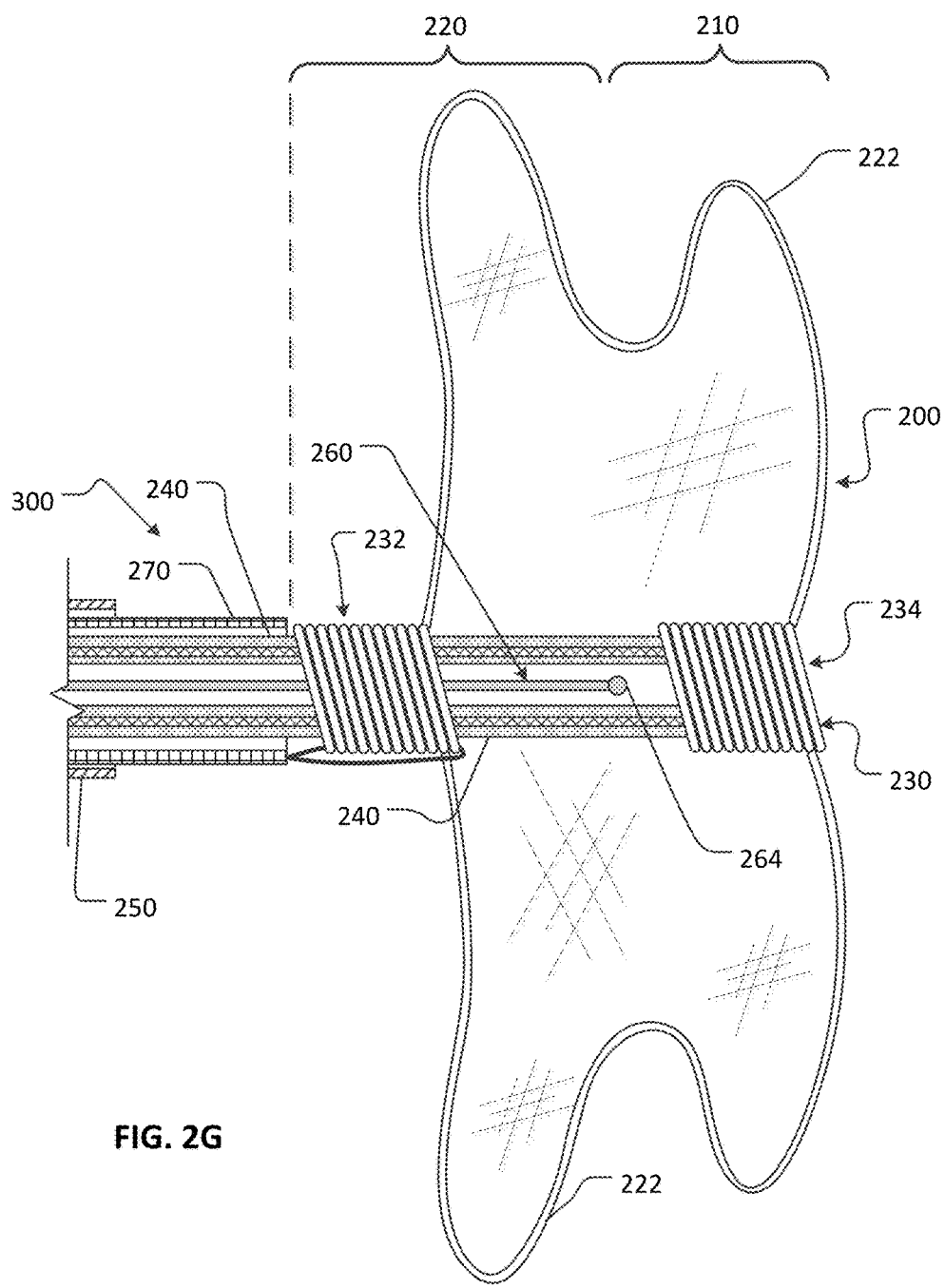

In reference to FIG. 2G, the inner wire 260 has been retracted from the elastomeric element 234 (not visible in FIG. 2G because it is located within a space defined by the distal eyelet 230, the distal eyelet 230 not being drawn in cross-section in FIGS. 2B-2G) of the distal eyelet 230. This step can be performed by the clinician operator when the clinician operator is satisfied with the positioning of the distal portion 210 of the medical device 200.

To remove the inner wire 260, the clinician operator can perform the following operations. First, the distal end of the inner catheter 240 can be positioned so that it abuts the proximal face of the elastomeric element 234 (refer to the enlarged view of FIG. 2A). Then, while holding the inner catheter 240 stationary, the clinician operator can pull (e.g., apply a proximally directed force to) the elongate element 262 of the inner wire 260. In some embodiments, since the inner wire 260 has a bulbous tip 264 that is larger than the through-hole 236 of the elastomeric element 234, the inner wire 260 may need to be pulled forcefully while also holding the inner catheter 240 stationary with some force to prevent movement in a proximal direction of the elastomeric element 234 and the distal eyelet 230. In some embodiments, the bulbous tip 264 is deformable to facilitate passage of the bulbous tip 264 through the through-hole 236 of the elastomeric element 234. In some embodiments, the bulbous tip 264 can be temporarily made to have a smaller profile to facilitate passage of the bulbous tip 264 through the through-hole 236 of the elastomeric element 234. For example, in some embodiments the bulbous tip 264 is inflatable and the bulbous tip 264 can be deflated to facilitate passage of the bulbous tip 264 through the through-hole 236 of the elastomeric element 234. In some embodiments, the bulbous tip 264 can be mechanically actuated to reduce the profile of the bulbous tip 264 to facilitate passage of the bulbous tip 264 through the through-hole 236 of the elastomeric element 234.

Various combinations of through-hole 236 diameters and shapes in relation to the outer peripheral size of the bulbous tip 264 can be used to arrive at desired amounts of proximally directed pulling forces or distally directed holding forces (e.g., to maintain a stationary position) that will cause the inner wire 260 to disengage from the elastomeric element 234. In addition, the material used for the elastomeric element 234 can affect the level of resistance provided by the elastomeric element 234 in response to pulling forces applied to the inner wire 260, and the material can be selected accordingly. In some embodiments, the through-hole 236 can also include slits (not shown) that radially extend from the center of the through-hole 236 to permit easier withdrawal of the inner wire 260 from the elastomeric element 234. Such design features can be incorporated to create a desired amount of pulling force required to disengage the inner wire 260 from the elastomeric element 234.

In some embodiments, the elastomeric element 234 includes features to provide tactile feedback to the clinician operator during withdrawal of the inner wire 260. For example, portions along the length of the through-hole 236 can have different diameters that can exert different resistances to the movement of the bulbous tip 264. In some embodiments, the variation in resistance to movement of the bulbous tip 264 can provide tactile feedback to the clinician operator to indicate the position of the bulbous tip 264 in relation to the elastomeric element 234 during the withdrawal process. In some embodiments, the elastomeric element 234 can have one or more internal open-spaces along the length of the through-hole 236. In such cases, the clinician operator can feel a release of resistance to movement as the bulbous tip 264 enters an internal open-space. In some embodiments having such internal open-spaces, the inner wire 260 and bulbous tip 264 can be pulled through a first portion of the elastomeric element 234, and then with the bulbous tip 264 in an internal open-space, the clinician operator can retain control of the attachment feature (e.g., distal eyelet 230) containing the elastomeric element 234.

In some embodiments, elastomeric element 234 is elastically deformed as the bulbous tip 264 is pulled through the through-hole 260. In some embodiments, elastomeric element 234 is irreversibly deformed (plastically deformed) as the bulbous tip 264 is pulled through the through-hole 260.

Because the clinician is satisfied with the positioning of the device prior to disengagement, it may be desirable to minimize or avoid any repositioning or relative movement of the device with respect to the deployment site during disengagement of the delivery system from the device. For example, as the inner wire 260 and bulbous tip 264 are withdrawn from the elastomeric element 234, in some embodiments it is desirable to minimize or prevent shifting or movement of the distal eyelet 230. In some embodiments, generally proximally directed forces exerted by the bulbous tip 264 on the elastomeric element 234 as the bulbous tip 264 is pulled through the channel or through-hole 236 of the elastomeric element 234 can be offset by an equal and opposite force applied by distal face of the inner catheter 240 against the elastomeric element.

Generally proximally directed forces can be transferred from the elastomeric element 234 to the inner catheter 240. In some embodiments, it is desirable for the inner catheter 240 to offset or counteract such forces so that the inner catheter is not longitudinally compressed, for example, and so that the distal eyelet 230 and distal portion 210 of the device are not displaced positionally in relation to surrounding tissue. In some embodiments, an actuator operable by the clinician operator can provide a mechanical advantage for pulling the inner catheter 240 so as to cause the bulbous tip 264 to pass through the through-hole 236 of the elastomeric element 234. For example, the actuator may include a lever (or other type of actuator) that can be permanently or temporarily coupled to the inner catheter 240 to provide a mechanical advantage for pulling the inner catheter 240.

In some embodiments, a reinforcement layer 242 is included in the inner catheter 240. As described above, the reinforcement layer 242 can add compressive rigidity (column strength) to the inner catheter 240. In other words, by adding a reinforcement layer 242, the inner catheter 240 may experience less longitudinal deflection when the inner catheter 240 is exposed to a compressive force caused by the pulling of the inner wire 260 (or by an inclination of the device 200, based on the shape memory property of the frame members, to assume the device's natural position when the device is being held in an elongated or constrained configuration, for example). With such compressive rigidity, the position of the distal eyelet 230 can be maintained substantially stationary as the inner wire 260 is pulled to cause the bulbous tip 264 to pass through the through-hole 236 of the elastomeric element 234. In this fashion, the inner wire 260 can be removed from engagement with the elastomeric element 234.

Figure 2H:
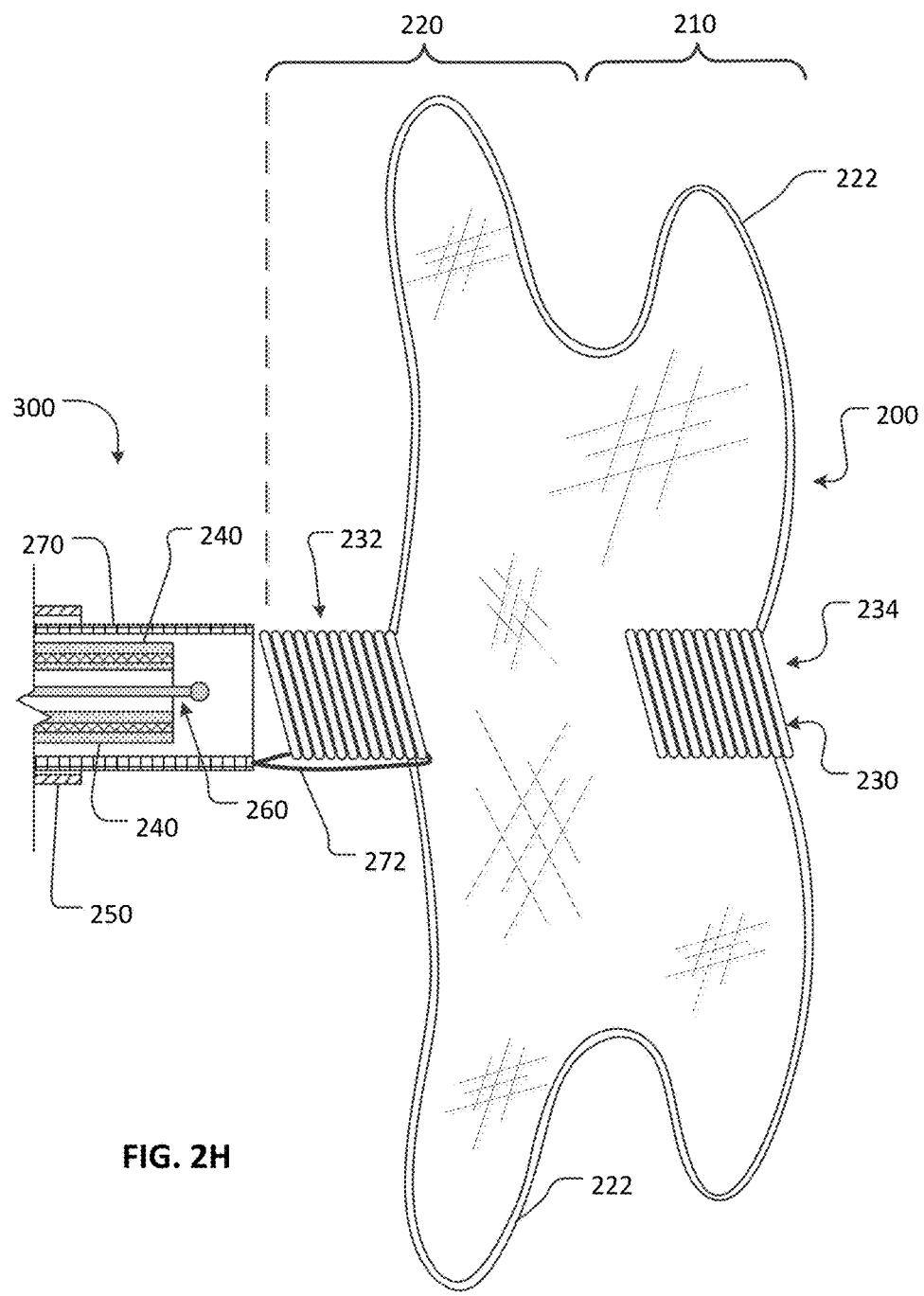
Figure 21:
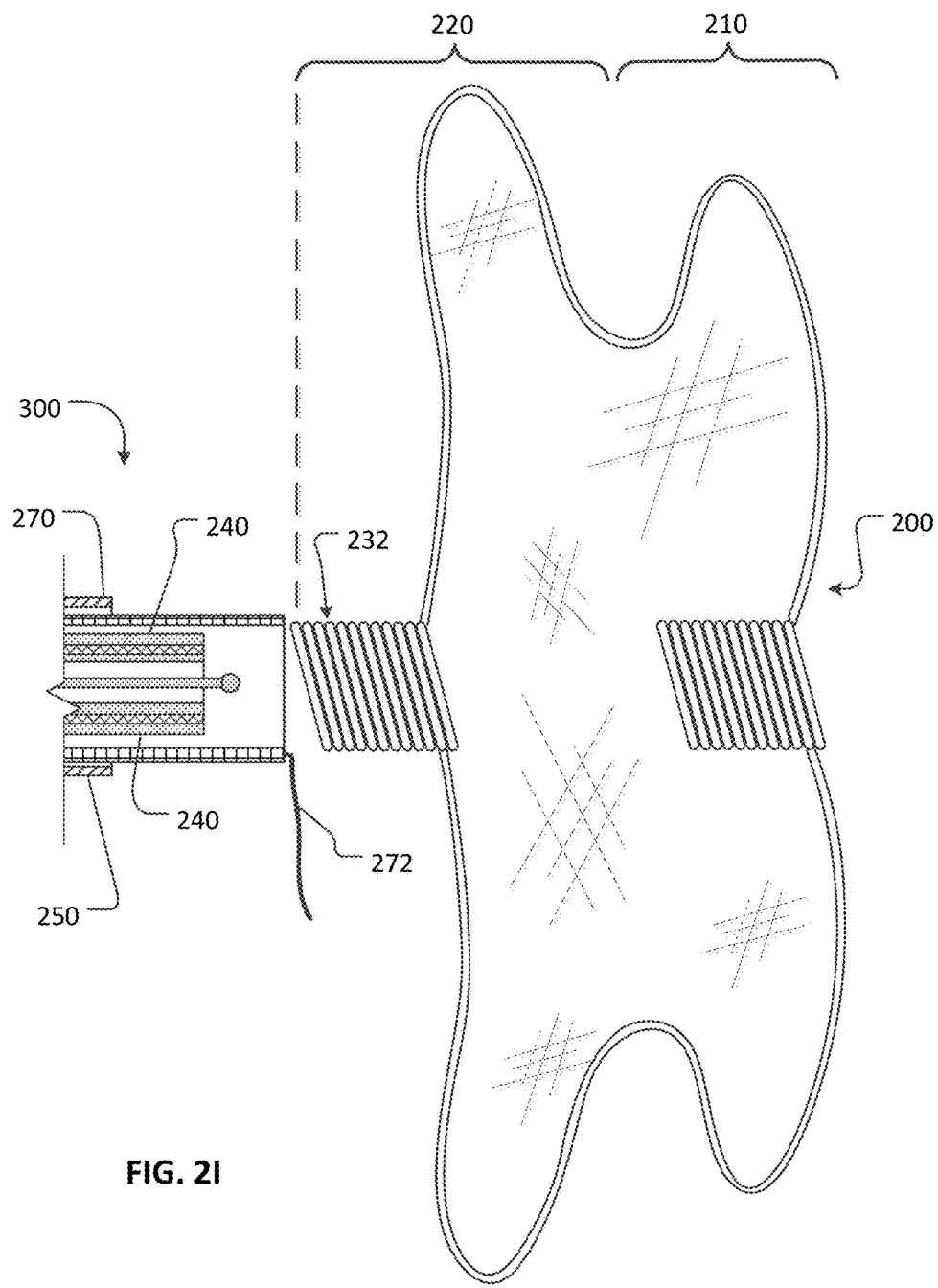

In reference to FIG. 2H, the inner catheter 240 and inner wire 260 have been retracted to disengage them from both eyelets 230 and 232 of the medical device 200. At this juncture, the only remaining attachments of the deployment system 300 to the medical device 200 is via the outer catheter 270, and via the suture tether 272 to the proximal eyelet 232.

Before releasing the suture tether 272 from the proximal eyelet 232, the clinician can assess the positioning of the proximal portion 220 of the medical device 200. As described above, visualization can be performed by MRI, x-ray, or other visualization systems, and radiopaque markers or materials can be included on portions of the medical device 200, such as on the frame elements 222 and/or eyelets 230 and 232. In this configuration as shown in FIG. 2H, the "backbone-like" influence of the inner catheter 240 on the eyelets 230 and 232 has been removed. Therefore, some natural repositioning of the proximal portion 220 may occur upon disengagement of the inner catheter 240 from the proximal eyelet 232. The clinician operator may therefore desire to reassess the positioning of the proximal portion 220 prior to releasing control of the proximal eyelet 232.

In some embodiments, to further simulate the position that the proximal portion 220 of the medical device 200 will assume after removal of the deployment system 300, the clinician operator may provide additional slack in the suture tether 272. In other words, in the configuration shown, the outer catheter 270 may provide some influence via the suture tether 272 to the position of the proximal eyelet 232. To simulate any future natural positioning of the proximal eyelet 232 and proximal portion 220 in relation to the surrounding tissue, the clinician can substantially remove the influence of the outer catheter 270 by slackening the suture tether 272, and, in some cases, retracting the outer catheter 270 by an amount to ensure that the outer catheter 270 is not contacting the medical device 200. After slackening the suture tether 272 and retracting the outer catheter 270, the clinician can assess the positioning of the proximal portion 220 in relation to the surrounding tissue.

If the clinician is dissatisfied with the positioning of the proximal portion 220, the clinician can re-extend the outer catheter 270 near the proximal eyelet 232, and retighten the suture tether 272 to reacquire positioning control of the proximal eyelet 232. The clinician operator can then reposition the proximal portion 220 as desired, and can subsequently repeat, if desired, the process described above to assess the resulting natural positioning of the proximal portion 220.

In some embodiments, the inner wire 260 can also be used to reposition the eyelets 230 and 232. In some embodiments, the inner wire 260 has a curved portion near the distal end of the inner wire 260. By manipulating the curved portion of the inner wire 260, the clinician operator can manipulate the position of the eyelets 230 and 232 using the curved portion like a hook. In some embodiments, for example when the inner wire 260 comprises NiTi, the inner wire 260 can have a curve in the distal portion of the inner wire 260 that has been heat-set to create curved shape-memory. In some embodiments, for example when the inner wire 260 comprises stainless steel, the inner wire 260 can have one or more curves in the distal portion of the inner wire 260 that has been created by plastic deformation of the distal portion of the inner wire 260. In some such cases, the clinician operator can induce the curve in the inner wire 260 by bending the inner wire 260 to suit the clinician's desired shape.

When the clinician operator is satisfied with the positioning of the proximal portion 220, the operator can remove the suture tether 272 from engagement with the proximal eyelet 232 as shown in FIG. 2I. To disengage the suture tether 272 from the proximal eyelet 232, the clinician operator can release one end of the suture tether 272 and pull on the other end of the suture tether 272 to draw a suitable length of the suture tether 272 out from the outer catheter 270. After drawing the suitable length of the suture tether 272 from the outer catheter 270, the configuration will look similar to FIG. 2I (with the suture tether 272 being disengaged from the proximal eyelet 232). At this juncture, the medical device 200 has been fully released from the deployment system 300.

Figure 2J:
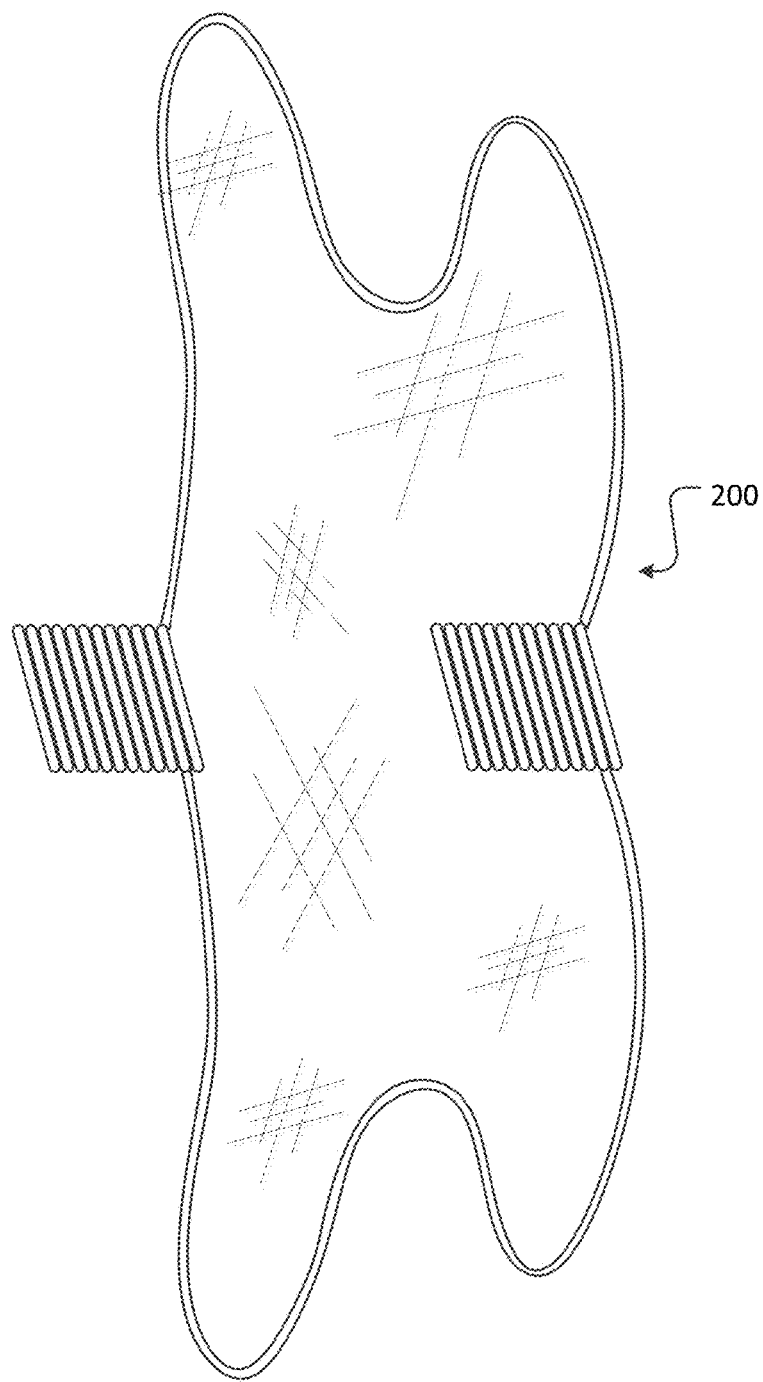

In reference to FIG. 2J, the final configuration of the medical device 200 is shown. This represents the medical device 200 as having been deployed from deployment system 300, in a controlled fashion, as described above in reference to FIGS. 2A-2I; and the deployment system 300 as having been removed from the vicinity of the deployment site.

As mentioned previously, distal eyelet 230 as depicted in FIGS. 2A-2I may be considered an inverted eyelet. In some embodiments, the deployment techniques described herein may be used with devices that do not include inverted eyelets. For example, device 100, which includes non-inverted distal eyelet 130 (see FIGS. 1A and 1B) could be deployed in a similar manner, with elastomeric member 234 positioned within distal eyelet 130. In some embodiments, the deployment techniques described herein may be used with devices that include one and only one eyelet, hub, or other type of attachment feature.

Elastomeric element 234 was depicted in FIG. 2A as located near the distal end of distal eyelet 230. In some embodiments, elastomeric element 234 is positioned nearer the center of the distal eyelet (e.g., eyelet 230 or 130), or nearer the proximal end of the distal eyelet (e.g., eyelet 230 or 130). Also, as discussed above, attachment features other than eyelets, including hubs and hooks, may be used. In some embodiments, elastomeric elements 234 can be utilized in more than one eyelet, e.g., a distal eyelet and a proximal eyelet. In some embodiments that include two or more eyelets (e.g., distal and proximal eyelets), elastomeric elements 234 can be utilized in just the proximal eyelet (e.g., eyelet 232 or 132). In some embodiments that include a single eyelet (or other type of attachment feature), elastomeric elements 234 can be used in the single eyelet (or other type of attachment feature).

Figure 3:
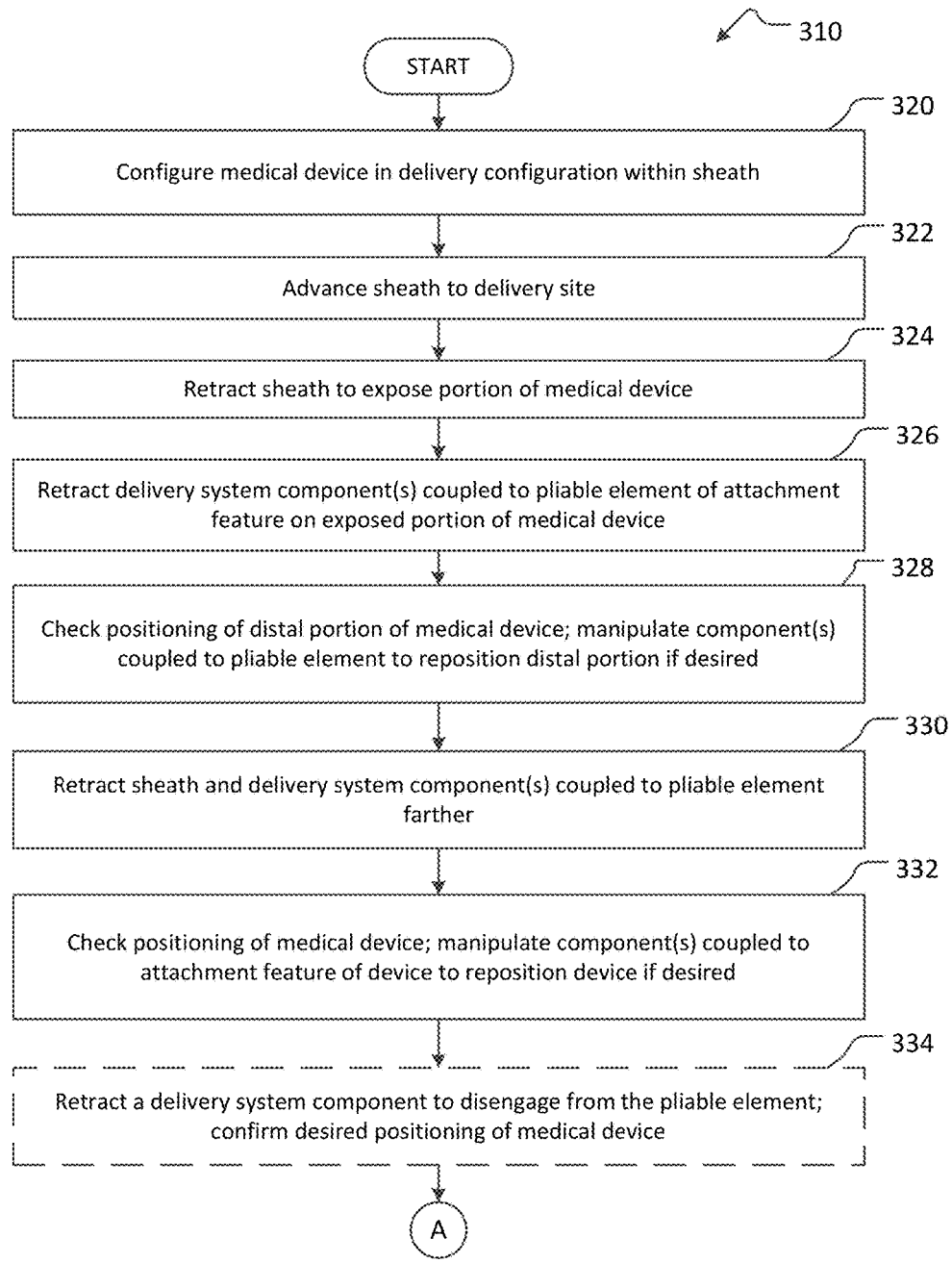
FIG. 3 is a flowchart of an example method for deploying an implantable medical device using the controllable deployment systems provided herein.

FIG. 3 is a flowchart of an example process 310 for deploying an implantable medical device using a deployment system embodying the features and techniques provided herein, such as the example deployment system 300 described above. In general, example process 310 pertains to a transcatheter process of deploying a medical device to a bodily cavity or vessel of a patient, as performed by a clinician operator.

At operation 320, an implantable medical device can be configured inside the sheath of a deployment system. In some embodiments, the medical device may be configured in a collapsed configuration to be placed within the sheath. In some embodiments, depending, for example, on the type of medical device, the medical device may not need to be collapsed to be placed within the sheath. In some embodiments of the medical device, an elastomeric element can be included as part of an attachment feature of the medical device.

Certain deployment system components can be included within the sheath. For example, in some embodiments, an inner catheter and an inner wire with a bulbous tip can be contained within the sheath. Further, in some embodiments, an outer catheter and suture tether are included within the sheath. Such deployment system components can be coupled to attachment features on the medical device, e.g., by attaching to an elastomeric element of an attachment feature.

The type of deployment system components to be included in the deployment system can depend on the type of medical device that is being deployed or on a preference of the clinician operator. For example, in some embodiments, the medical device may include two or more attachment features (e.g., as in the case of example medical device 200 described above). In some embodiments, the medical device being deployed includes only one attachment feature. In that case, the deployment system can include the components as required to suit the single attachment feature of the medical device.

At operation 322, the sheath containing the medical device can be advanced within the patient's body to a deployment site. In some embodiments, the sheath is steerable to assist the routing of the sheath to the deployment site. In some embodiments, other devices, such as guidewires and other catheters, can be used to assist the process of routing of the sheath to the deployment site. MRI, x-ray, ultrasound, and other types of visualization systems can be utilized to assist with the performance of routing the sheath to the deployment site. At the end of operation 322, the sheath containing the medical device is positioned at the deployment site as desired by the clinician operator, and the deployment of the medical device from the sheath can begin.

At operation 324, the sheath can be retracted a distance sufficient to expose at least part of the implantable medical device, e.g., a distal portion of the medical device. In some embodiments, it is desirable to position a distal portion of the medical device within the bodily cavity or vessel prior to the deployment of the remaining portions of the medical device.

At operation 326, the deployment system components that are releasably coupled to an elastomeric element of an attachment feature on the exposed portion of the medical device can be retracted a suitable distance. In some embodiments, the distance is predetermined. In some embodiments, the deployment system components that are releasably coupled to the elastomeric element may include an inner catheter and an inner wire with a bulbous tip. The action of retracting such deployment system components permits contacting of the exposed portion of the medical device with the surrounding tissue. In some cases, the exposed portion of the medical device self-expands so as to make contact with the surrounding tissue.

At operation 328, the clinician operator can use a visualization system (e.g., MRI, x-ray, ultrasound) to confirm the desirability of the positioning of the exposed portion of the medical device in relation to the surrounding tissue. In some cases, the clinician may wish to assess the seal provided between the periphery of the medical device and the surrounding tissue, as well as assessing the general positioning and orientation of the medical device in relation to particular features of the patient's anatomy. If the clinician operator is dissatisfied with the positioning, the clinician operator can reposition the exposed portion of the medical device by manipulating the components that are coupled to the elastomeric element of the attachment feature on the exposed portion of the medical device. Step 328 can be repeated until the clinician operator is satisfied with the positioning of the exposed portion of the medical device.

The clinician operator can, optionally, tug on the deployment system components that are coupled to the elastomeric element of the attachment feature on the exposed portion to assess the anchorage strength of the distal portion to the surrounding tissue. In this operation, the clinician operator may receive tactile feedback indicating either that the anchorage strength is satisfactory, or that the anchorage strength is unsatisfactory. If the anchorage strength is deemed unsatisfactory, the clinician operator can reposition the exposed portion of the medical device by manipulating the deployment system components that are coupled to the elastomeric element of the attachment feature on the exposed portion of the medical device. After such repositioning, assessing the anchorage strength of the medical device can be repeated until the clinician operator is satisfied with the anchorage strength of the exposed portion of the medical device.

At 330, the clinician operator can retract the sheath and deployment system components that are coupled to the elastomeric element farther. This can expose the remaining portions of the medical device, e.g., the proximal portions of the medical device. The remaining portions of the medical device may be permitted to make contact with surrounding tissue as a result of this operation. In some embodiments, the now exposed portions of the medical device may self-expand to make contact with the surrounding tissue.

At operation 332, the clinician operator can use a visualization system (e.g., MRI, x-ray, ultrasound) to confirm the desired positioning of the portion (e.g., proximal portion) of the medical device that was exposed from the sheath at operation 330. Further, the clinician operator can reposition the portion by manipulating deployment system components that are coupled to an attachment feature on that portion of the medical device. For example, in some embodiments an outer catheter of the deployment system can be tethered to an attachment feature on a proximal portion of the medical device. The clinician operator can, in such cases, manipulate the outer catheter to reposition the portion of the medical device. After repositioning, assessing the positioning of the portion of the medical device in relation to the surrounding tissue can be repeated until the clinician operator is satisfied with the position of the portion of the medical device.

At operations 334 and 336, a component that is releasably coupled to the elastomeric element can, optionally, be retracted to at least temporarily decouple that component from the elastomeric element. For example, the inner catheter can be retracted to decouple the inner catheter from the elastomeric element of a distal eyelet. Decoupling the deployment system component from the elastomeric element can remove the influence that the deployment system component may be exerting on the position of the medical device. With the deployment system component decoupled from the elastomeric element, the clinician operator can again assess the positioning of the medical device in relation to the surrounding tissue. If the positioning is satisfactory, the decoupled deployment system component can be re-coupled to the elastomeric element, and operation 336 is complete. However, if the position is not satisfactory, the decoupled deployment system component can be re-coupled to the elastomeric element (336), and the clinician operator can reposition the medical device by manipulating the deployment system components that are coupled to the elastomeric element. After such repositioning, operations 334 and 336 can be optionally repeated until the clinician operator is satisfied with the positioning of the medical device in relation to the surrounding tissue.

At operation 338, the deployment system components can be de-coupled from the elastomeric element that is included in an attachment feature of the medical device. For example, an inner catheter and an inner wire with a bulbous tip can be de-coupled from an elastomeric element. The clinician operator can de-couple the components from the elastomeric element, for example, by pulling the elongate element of the inner wire while holding the inner catheter stationary. This may cause the bulbous tip to be pulled proximal of, and disengaged from, the elastomeric element.

At operation 340, the deployment system components that were de-coupled from the elastomeric element can be further retracted, such that they are fully retracted from engagement with the medical device. For example, the inner wire and inner catheter can be retracted from engagement with both the distal eyelet and proximal eyelet of the medical device.

At operation 342, the clinician operator can, optionally, retract a deployment system component that is still coupled to the medical device while maintaining the coupling between the component and the medical device. For example, the suture tether can be slackened and the outer catheter can be retracted from the proximal eyelet.

At operation 344, the clinician operator can reassess the positioning and anchorage of the medical device, and can reposition the medical device if desired using the deployment system component that is still coupled to the medical device. For example, the clinician can use a visualization system and tactile feedback to confirm the positioning and anchorage strength of the medical device in relation to surrounding tissue, as by manipulating the outer catheter that is coupled to the proximal eyelet via the suture tether.

At operation 346, all remaining deployment system components that are coupled to the medical device can be decoupled from the medical device. At operation 348, the deployment system can be removed from the deployment site, leaving the implantable medical device in position at the deployment site as desired by the clinician operator.

Figure 4:
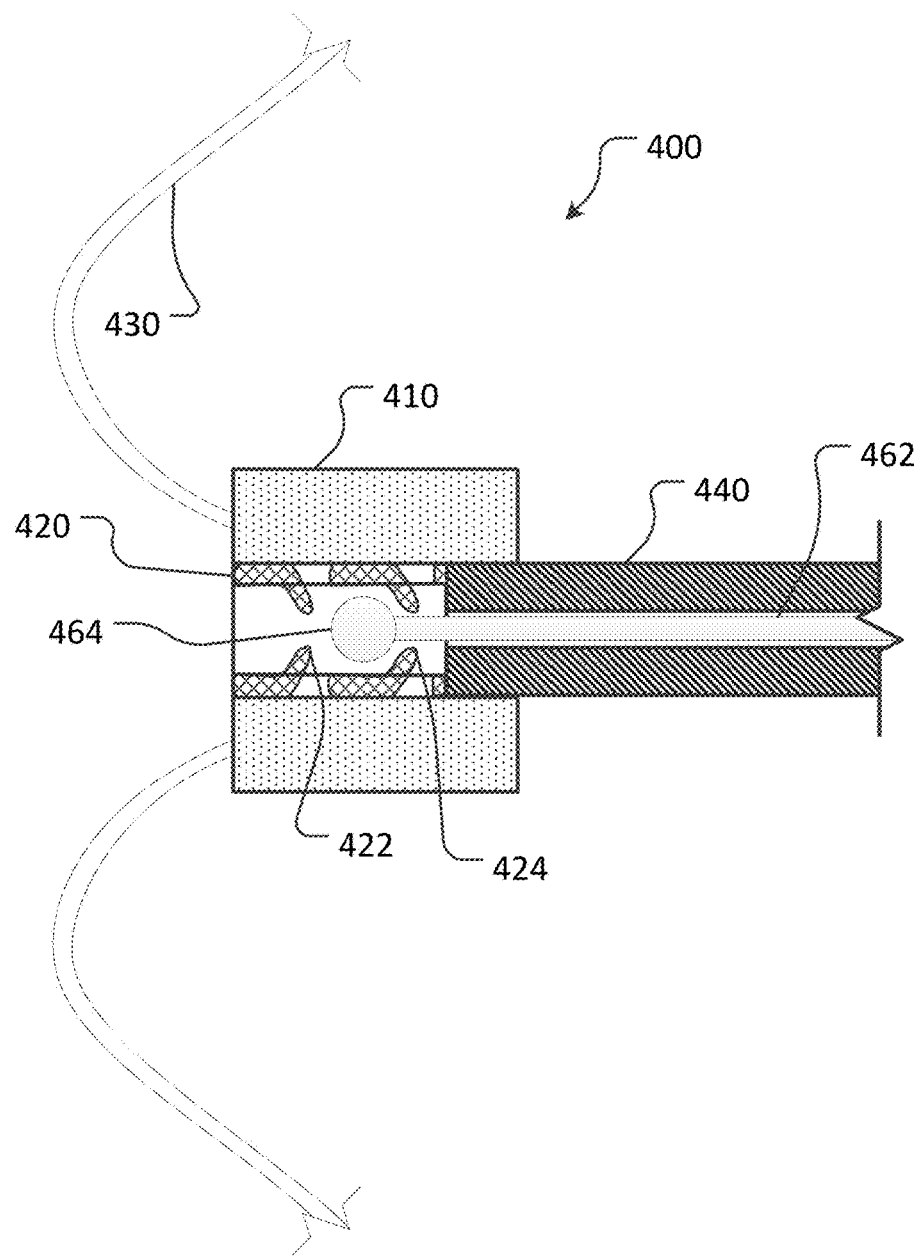
FIG. 4 depicts another example medical device attachment feature for use with a controllable deployment system.

FIG. 4 provides another example attachment feature 400 for use with the controllable deployment devices and method provided herein. In general, the attachment feature includes a hub 410 (which could also be an eyelet), and a deformable insert 420 coupled to the hub 410. The deployment system components shown include an inner catheter 440 and an elongate element 462 with a bulbous tip 464. While the hub 410 is depicted as a distal hub 410 of an implantable medical device, the example attachment feature 400 can also be used in the context of a proximal hub (such as eyelet 132 of FIG. 1B).

Frame elements 430 can extend from the hub 410. For clarity, the extended lengths of only two frame members 430 are shown, but more and/or fewer frame members 430 are envisioned. In some embodiments, hub 410 is a component that the frame members 430 are coupled to. In some embodiments, hub 410 is an eyelet that is formed from the coiled end portions of frame members 430.

The hub 410 of one or more attachment features 400 of an implantable medical device can include the deformable insert 420. The deformable insert 420 can be used advantageously for releasably coupling components of the deployment system to the attachment feature 400. That is, the deformable insert 420 of the attachment feature 400 can enable control of the attachment feature 400 via the coupling of the medical device to the deployment system. Deformable insert 420 can also facilitate the de-coupling of the deployment system from the attachment feature 400 by deforming the deformable insert 420 when the clinician operator desires to decouple the deployment system 400 from the medical device.

For example, in some embodiments the hub 410 of an implantable medical device includes a deformable insert 420 that is fixedly coupled to the attachment feature 400, e.g., deformable insert 420 can be fixedly coupled within a central bore of the hub 410. That is, in some embodiments the deformable insert 420 remains permanently coupled to the medical device after the release of the medical device from the deployment system. In that arrangement, the deformable insert 420 remains implanted in the patient as an integral component of the medical device. In some embodiments, the deformable insert 420 is fixedly coupled to the delivery device, and releasably coupled to the attachment feature 400 of the implantable medical device.

In some embodiments, the deformable insert 420 includes first tabs 422 and second tabs 424. In some embodiments, the tabs 422 and 424 act as barriers to temporarily restrain the bulbous tip 464 between the tabs 422 and 424, as described further below. In some embodiments, two or more elastomeric elements with through-holes (as described above) can be substituted for the deformable insert 420 with tabs 422 and 424. In some such embodiments, the bulbous tip 464 can reside between the elastomeric elements in a manner similar to the arrangement shown with the bulbous tip residing between the tabs 422 and 424.

In some embodiments, the deformable insert 420 is made from a nitinol tube that has been laser-cut to create tabs 422 and 424. After the tabs 422 and 424 are cut in the nitinol tube, the tabs can be displaced radially inward, as shown in FIG. 4, and heat-set so that the deformable insert 420 retains the configuration having tabs 422 and 424 deflected towards the interior of the deformable insert 420. In some embodiments, other materials (e.g., stainless steel, other metals, polymeric materials, or combinations of such materials) are used to construct the deformable insert 420. The deformable insert 420 can be attached to the hub 410 in various manners, e.g., by press-fitting, welding, adhering, and the like. The tabs 422 and 424 are deformable in the proximal direction so that the bulbous tip 464 can pass through the tabs 422 and 424 in a proximal direction under certain conditions. In some embodiments, the tabs 422 and 424 are configured to prevent the bulbous tip 464 from passing through the tabs 422 and 424 in a distal direction.

The force required to pull the bulbous tip 464 past the tabs 422 and 424 in the proximal direction can be established as desired by determining various design parameters of the deformable insert 420 that effect the release force of the attachment feature 400. For example, such design parameters include, but are not limited to, the type of material used for the tabs 422 and 424, the bend-angles of the tabs 422 and 424, the thicknesses of the tabs 422 and 424, and the width of the tabs 422 and 424. In some embodiments, tab 422 has different design parameters than tab 424. In some embodiments, tabs 422 and 424 have substantially similar design parameters. The design parameters of the tabs 422 and 424 can be selected to create a deployment system with the release force properties as desired. In some embodiments, the force to pull the bulbous tip 464 beyond tab 424 in the proximal direction can be established at a high enough level of force to allow the clinician operator to tug on the elongate element 462 without pulling the bulbous tip 464 proximally past tab 424. The tugging action can serve to seat the medical device with the tissue at the deployment site. If the medical device includes anchoring devices, the tugging action can serve to embed the anchoring devices on the medical device into tissue at the deployment site.

In some embodiments, the arrangement shown in FIG. 4, wherein the bulbous tip 464 is arranged between the first tabs 422 and the second tabs 424, is advantageously used to controllably deploy a medical device using attachment feature 400. To arrive at the arrangement shown, in some embodiments the elongate element 462 is loaded into the medical device from the distal end of the hub 410. The elongate element 462 can be pushed proximally through the hub 410 until the bulbous tip 464 is positioned near the hub 410. Then the proximal end of the elongate element 462 can be pulled (while the inner catheter 440 is held stationary) so that the bulbous tip 464 causes a radial outward deflection of the first tabs 422. The deflection of the first tabs 422 can allow the bulbous tip 464 to pass by the first tabs 422 such that the bulbous tip 464 resides between the first tabs 422 and the second tabs 424. The inner catheter 440 can be held stationary to provide column strength to resist proximal movement of the hub 410 as the elongate element 462 is pulled proximally. In that fashion, the inner catheter 400 can hold the hub 410 from being pulled proximally as the elongate element 462 is pulled proximally. In some embodiments, rather than proximally pulling the elongate element 462 to make the bulbous tip pass beyond the first tabs 422, the bulbous tip 464 can be pushed proximally to make the bulbous tip 464 pass beyond the first tabs 422. Or, in some embodiments, a combination of such methods can be used.

In the configuration shown (wherein the bulbous tip 464 is between the tabs 422 and 424), the medical device can be loaded into a delivery catheter (not shown) for controllable deployment as described in reference to FIGS. 2A-2J. In some embodiments, the deformable insert 420 performs analogously to the elastomeric element 234. In some embodiments, the deformable insert 420 contains the bulbous tip 464 so that the bulbous tip 464 is hindered from moving distally in relation to the hub 410. An advantage of this feature is that the bulbous tip 464 will not protrude from the hub 410 in which case it could potentially damage tissue.

When the clinician operator performing the medical device implant procedure is ready to release the attachment feature 400, the elongate element 462 can be pulled proximally while holding the inner catheter 440 substantially stationary. The bulbous tip 464 will be pulled past the second tabs 424 because the force exerted on the second tabs 424 from the bulbous tip 464 will cause the second tabs 424 to deflect outwardly in a radial direction. The outward radial deflection of the second tabs 424 will allow the bulbous tip 464 to pass by in a proximal direction. In this manner the elongate element 462 can be decoupled from the attachment feature 400, and the medical device can be controllably deployed.

For additional examples of medical devices that can use the deployment system features described herein, see the provisional patent application titled "Space Filling Devices," having inventors Coby C. Larsen, Brandon A. Lurie, Steven J. Masters, Thomas R. McDaniel, and Stanislaw L. Zukowski, filed on 16 Nov. 2012, assigned U.S. Ser. No. 61/727,458 and the provisional patent application titled "Space Filling Devices," having inventors Coby C. Larsen, Brandon A. Lurie, Steven J. Masters, Thomas R. McDaniel, and Stanislaw L. Zukowski, filed on 15 Mar. 2013, the disclosures of which are considered part of and are specifically incorporated by reference in their entirety (including the figures) for all purposes in the present disclosure.

For additional examples of medical devices that can use the deployment system features described herein, see the provisional patent application titled "Joint Assembly for Medical Devices," having inventors Coby C. Larsen, Steven J. Masters, and Thomas R. McDaniel, filed on 16 Nov. 2012, assigned U.S. Ser. No. 61/727,328 and the non-provisional patent application titled "Joint Assembly for Medical Devices," having inventors Coby C. Larsen, Steven J. Masters, and Thomas R. McDaniel, filed on 15 Mar. 2013, the disclosures of which are considered part of and are specifically incorporated by reference in their entirety (including the figures) for all purposes in the present disclosure.

While this specification contains many specific implementation details, these should not be construed as limitations on the scope of any devices, methods, and systems discussed herein, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Particular embodiments of the subject matter have been described. Other embodiments are within the scope of the following claims.

What is claimed is:

1. A medical device delivery system, comprising:
an implantable medical device including frame members extending from a proximal end of the implantable device to a distal end of the implantable medical device, a plurality of fixation anchors arranged on bend regions of the frame members, a covering arranged with the frame members, and a first attachment feature disposed near the distal end of the device and a second attachment feature disposed near the proximal end of the device, wherein the first attachment feature includes an elastomeric element having a channel, and the implantable medical device tapers between the proximal end and the distal end of the implantable device; and
a delivery device including a first catheter that is arranged to contact the elastomeric element and sized to pass through the first attachment feature and configured to apply torque to the first attachment feature and the second attachment feature with each of the first attachment feature and the second attachment feature being keyed to the first catheter to prevent rotation of the first and the second attachment features in relation to the first catheter, and wherein the delivery device includes an elongate element having a bulbous tip at the distal end, that is arranged to releasably couple with the elastomeric element, wherein the first catheter and the elongate element are independently controllable to position the first attachment feature and wherein the elastomeric element comprises first tabs and second tabs on opposing sides of the channel configured to elastically deform in response to pulling the bulbous tip in a direction proximal to the elastomeric element.

2. The medical device delivery system of claim 1, wherein the channel that extends in an axial direction through the elastomeric element, and wherein the first tabs and the second tabs are further configured to pass the bulbous tip by the first tabs in response to pulling the bulbous tip in a direction proximal to the elastomeric element.

3. The medical device delivery system of claim 2, wherein the first tabs and the second tabs are configured to prevent the bulbous tip from passing through the first tabs and the second tabs in response to pushing the elongate member in direction distal to the elastomeric element.

4. The medical device delivery system of claim 3, wherein the bulbous tip is adapted to pass through the channel.

5. The medical device delivery system of claim 1, comprising a delivery sheath, and wherein the implantable medical device and the delivery device are capable of being located in one or more lumens of the delivery sheath.

6. The medical device delivery system of claim 5, further comprising a deployment actuator coupled to the delivery device and to the delivery sheath, and wherein the deployment actuator is adapted to control positioning of the implantable medical device.

7. The medical device delivery system of claim 1, wherein the elastomeric element is fixedly attached to at least one of the first attachment feature and the second attachment feature.

8. The medical device delivery system of claim 1, wherein a distal end of the first catheter is arranged to abut against the elastomeric element.

9. The medical device delivery system of claim 1, wherein the second attachment feature comprises an aperture through which the first catheter passes.

10. The medical device delivery system of claim 1, wherein the delivery device includes a second catheter adapted to releasably couple with the second attachment feature.

11. The medical device delivery system of claim 10, wherein the first catheter and the second catheter are arranged coaxially.

12. The medical device delivery system of claim 11, wherein the elongate element is arranged coaxially with the first and second catheters.

13. A medical device delivery system, comprising:
an implantable medical device having frame members extending from a proximal end of the implantable device to a distal end of the implantable medical device, a plurality of fixation anchors arranged on bend regions of the frame members, a covering arranged with the frame members, and a first attachment feature disposed near a distal end of the device and a second attachment feature disposed near a proximal end of the device, wherein the attachment features includes an elastomeric element that is fixedly attached to the first attachment feature, and wherein the elastomeric element includes a channel that extends in an axial direction through the elastomeric element, and wherein the implantable medical device tapers between the proximal end and the distal end of the implantable device; and
a delivery device including a catheter with a distal end that is arranged to abut the elastomeric element and sized to pass through the first attachment feature and configured to apply torque to the first attachment feature and the second attachment feature with each of the first attachment feature and the second attachment feature being keyed to the first catheter to prevent rotation of the first and the second attachment features relative to the first catheter, and wherein the delivery device includes an elongate element located substantially coaxially within the catheter, wherein the elongate element includes a bulbous distal tip that is arranged to releasably couple with the elastomeric element and wherein the catheter and the elongate element are independently controllable to position the first attachment feature, and wherein the elongate element is adapted to pass through the channel and configured to elastically deform in response to pulling the bulbous tip in a direction proximal to the elastomeric element.

14. The medical device delivery system of claim 13, further comprising a delivery sheath, and wherein the implantable medical device and the delivery device are capable of being located in one or more lumens of the delivery sheath.

15. The medical device delivery system of claim 14, further comprising a deployment actuator coupled to the delivery device and to the delivery sheath, and wherein the deployment actuator is adapted to control positioning of the implantable medical device.

* * * * *